(12) United States Patent
Green et al.

(10) Patent No.: US 12,618,098 B2
(45) Date of Patent: May 5, 2026

(54) PROXIMITY-DRIVEN ACTIVATION OF CRISPR-Cas SYSTEMS FOR DETECTION OF DIVERSE MOLECULAR ANALYTES

(71) Applicant: Arizona Board of Regents on behalf of Arizona State University, Scottsdale, AZ (US)

(72) Inventors: Alexander Green, Boston, MA (US); Kirstie Swingle, Phoenix, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 1138 days.

(21) Appl. No.: 17/606,225

(22) PCT Filed: Apr. 27, 2020

(86) PCT No.: PCT/US2020/030032
§ 371 (c)(1),
(2) Date: Oct. 25, 2021

(87) PCT Pub. No.: WO2020/220013
PCT Pub. Date: Oct. 29, 2020

(65) Prior Publication Data

US 2022/0403444 A1 Dec. 22, 2022

Related U.S. Application Data

(60) Provisional application No. 62/976,659, filed on Feb. 14, 2020, provisional application No. 62/839,050, filed on Apr. 26, 2019.

(51) Int. Cl.
*C12Q 1/6804* (2018.01)
*C12N 9/22* (2006.01)
*C12N 15/11* (2006.01)

(52) U.S. Cl.
CPC ............ *C12Q 1/6804* (2013.01); *C12N 9/22* (2013.01); *C12N 15/11* (2013.01); *C12N 2310/20* (2017.05)

(58) Field of Classification Search
CPC ...... C12Q 1/6804; C12Q 1/6813; C12N 9/22; C12N 15/11; C12N 2310/20
See application file for complete search history.

(56) References Cited

U.S. PATENT DOCUMENTS

2018/0100189 A1 4/2018 Fredriksson

FOREIGN PATENT DOCUMENTS

NO 2019051318 A1 3/2019

OTHER PUBLICATIONS

Kellner (Nature Protocols vol. Oct. 14, 2014 pp. 2986-3012).*
Li et al. (BioRxix, 2019, pp. 1-7).*
(Continued)

*Primary Examiner* — Sarae L Bausch
(74) *Attorney, Agent, or Firm* — Quarles & Brady LLP

(57) ABSTRACT

Provided herein are methods and compositions for rapid, highly sensitive detection of molecular analytes such as antibodies, proteins, and small molecules using protein-driven nucleic acid assemblies to activate CRISPR-Cas nucleases. Also provided herein are uses of the sensitive analyte detection methods in an analyte detection platform and in convenient low-cost diagnostic assays such as lateral flow devices for point-of-care use.

9 Claims, 18 Drawing Sheets

(56) References Cited

OTHER PUBLICATIONS

Liu (Biosensors and Bioelectronics, 2018, vol. 102, pp. 204-210).*
Barletta, J. M., et al. "Lowering the detection limits of HIV-1 viral load using real-time immuno-PCR for HIV-1 p24 antigen." American journal of clinical pathology 122.1 (2004): 20-27.
Barrangou, R. et al. A decade of discovery: CRISPR functions and applications. Nat. Microbiol. 2, 17092 (2017).
Barrangou, R. et al. CRISPR Provides Acquired Resistance Against Viruses in Prokaryotes. Science (80-. ). 315, (2007).
Chen, J. S. et al. CRISPR-Cas12a target binding unleashes indiscriminate single-stranded DNase activity. Science (80-. ). 360, (2018).
Dong, D. et al. The crystal structure of Cpf1 in complex with CRISPR RNA. Nature 532, 522-526 (2016).
Doudna, J. A. et al. The new frontier of genome engineering with CRISPR-Cas9.
Engelen, W., et al. Antibody-controlled actuation of DNA-based molecular circuits. Nat. Commun. 8, (2017).
Fakhry, C. et al. Serum antibodies to HPV16 early proteins warrant investigation as potential biomarkers for risk stratification and recurrence of hpv-associated oropharyngeal cancer. Cancer Prev. Res. 9, 135-141 (2016).
Fonfara, I., et al. The CRISPR-associated DNA-cleaving enzyme Cpf1 also processes precursor CRISPR RNA. Nature 532, 517-521 (2016).
Gao, P., et al. Type v CRISPR-Cas Cpf1 endonuclease employs a unique mechanism for crRNA-mediated target DNA recognition. Cell Res. 26, 901-913 (2016).
Gootenberg, J. S. et al. Nucleic acid detection with CRISPR-Cas13a/C2c2. Science (80-. ). 356, 438-442 (2017).
Gray, E. R. et al. Unravelling the Molecular Basis of High Affinity Nanobodies against HIV p24: In Vitro Functional, Structural, and in Silico Insights. ACS Infect. Dis. 3, 479-491 (2017).
International Searching Authority. International Search Report and Written Opinion for application PCT/US2020/030032. Mailed on Oct. 6, 2020.
Koonin, E. V, et al. Diversity, classification and evolution of CRISPR-Cas systems. Curr. Opin. Microbiol. 37, 67-78 (2017).
Liu, W., et al. "Polymerase Spiral Reaction (PSR): A novel isothermal nucleic acid amplification method." Scientific reports 5.1 (2015): 1-8.
Lundberg, M., et al. "Homogeneous antibody-based proximity extension assays provide sensitive and specific detection of low-abundant proteins in human blood." Nucleic acids research 39.15 (2011): e102-e102.
Marraffini, L. A. et al. CRISPR Interference Limits Horizontal Gene Transfer in Staphylococci by Targeting DNA. Science (80-. ). 322, 1843-1845 (2008).
Mcgregor, L. M., et al. Interaction-dependent PCR: Identification of ligand-target pairs from libraries of ligands and libraries of targets in a single solution-phase experiment. J. Am. Chem. Soc. 132, 15522-15524 (2010).
Meyer, A. J., et al. "Escherichia coli "Marionette" strains with 12 highly optimized small-molecule sensors." Nature chemical biology 15.2 (2019): 196-204.
Myhrvold, C. et al. Field-deployable viral diagnostics using CRISPR-Cas13.
Schallmeiner, E. et al. Sensitive protein detection via triple-binder proximity ligation assays. Nat. Methods 4, 135-137 (2007).
Shah, S. A., et al. "Protospacer recognition motifs: mixed identities and functional diversity." RNA biology 10.5 (2013): 891-899.
Singh, D. et al. Real-time observation of DNA target interrogation and product release by the RNA-guided endonuclease CRISPR Cpf1 (Cas12a). Proc. Natl. Acad. Sci. 115, 5444-5449 (2018).
Söderberg, O. et al. Direct observation of individual endogenous protein complexes in situ by proximity ligation. Nat. Methods 3, 995-1000 (2006).
Stella, S., et al. Structure of the Cpf1 endonuclease R-loop complex after target DNA cleavage. Nature 546, 559-563 (2017).
Swarts, D. C., et al. Structural Basis for Guide RNA Processing and Seed-Dependent DNA Targeting by CRISPR-Cas12a. Mol. Cell 66, 221-233.e4 (2017).
Tang, X. et al. A CRISPR-Cpf1 system for efficient genome editing and transcriptional repression in plants. Nat. Plants 3, 17018 (2017).
Yamano, T. et al. Crystal Structure of Cpf1 in Complex with Guide RNA and Target DNA. Cell 165, 949-962 (2016).
Zetsche, B. et al. Cpf1 Is a Single RNA-Guided Endonuclease of a Class 2 CRISPR-Cas System. Cell 163, 759-771 (2015).

* cited by examiner

Figures 2A, 2B:
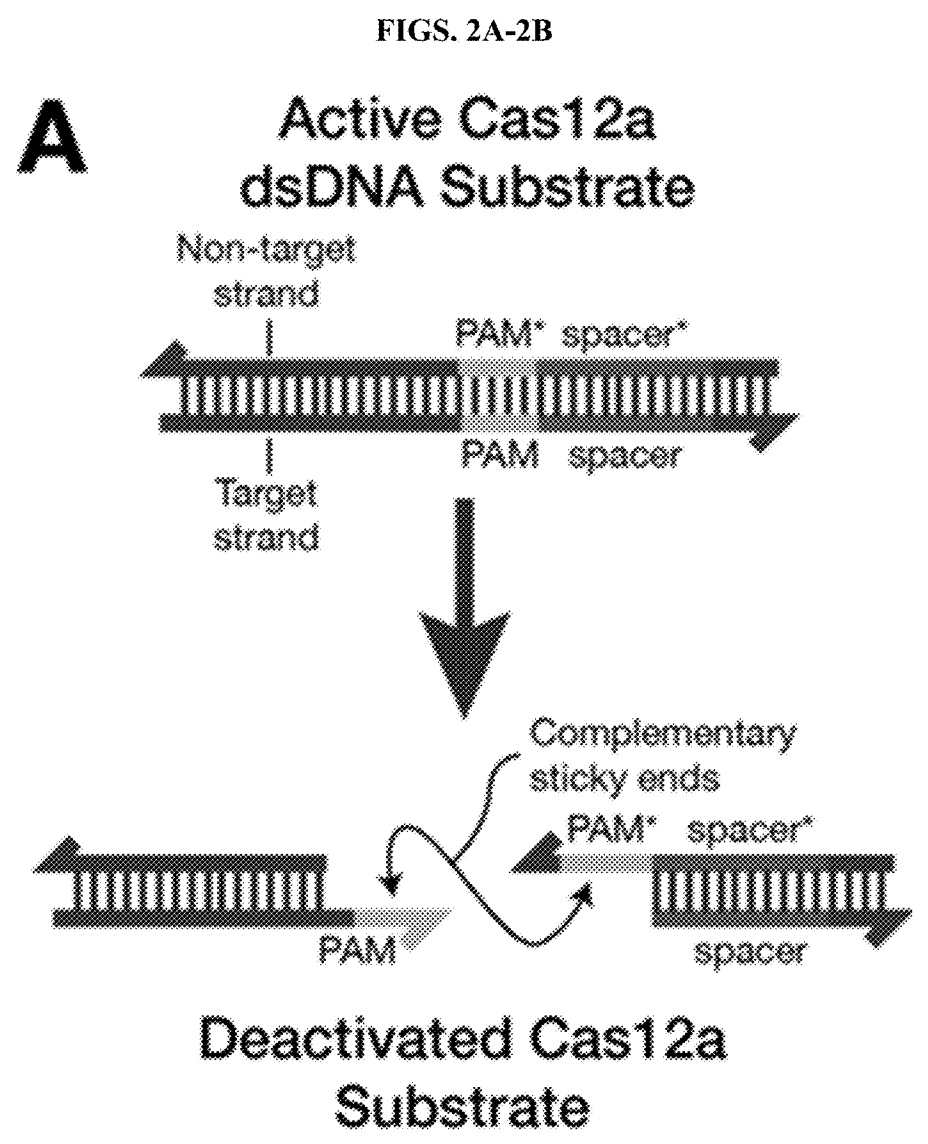

Active Cas12a
dsDNA Substrate

Non-target strand

PAM* spacer*

PAM spacer

Target strand

Complementary sticky ends

PAM* spacer* spacer

PAM

Deactivated Cas12a
Substrate

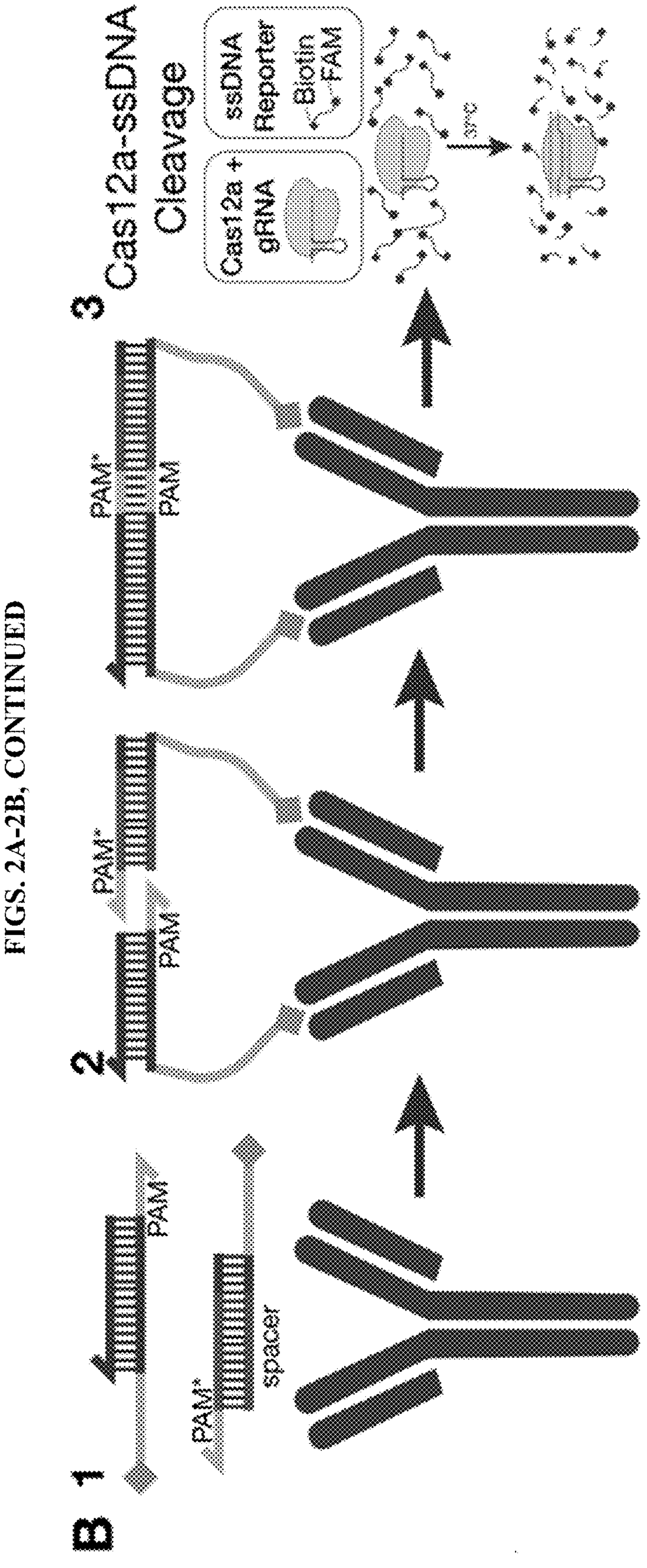
FIGS. 2A-2B, CONTINUED

Figure 3A:
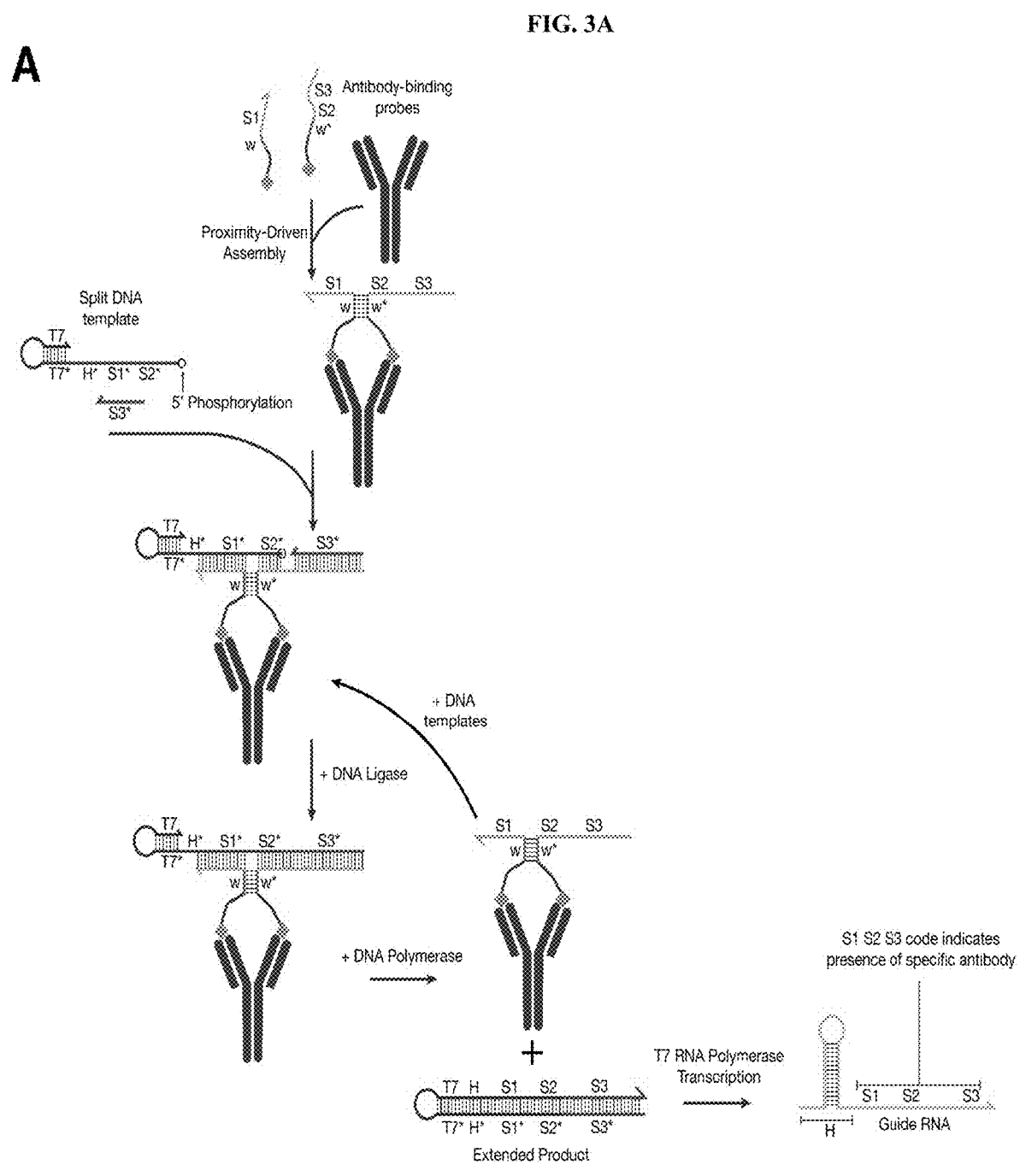

Antibody-binding probes
S3
S2
w*
S1
w
Proximity-Driven Assembly
S1 S2 S3
w w*
Split DNA template
T7
T7* H* S1* S2*
S3*
5' Phosphorylation
T7 H* S1* S2* S3*
T7*
w w*
+ DNA templates
+ DNA Ligase
S1 S2 S3
w w*
T7 H* S1* S2* S3*
T7*
w w*
+ DNA Polymerase
+
S1 S2 S3 code indicates presence of specific antibody
T7 RNA Polymerase Transcription
T7 H S1 S2 S3
T7* H* S1* S2* S3*
Extended Product
S1 S2 S3
H
Guide RNA

Design 2

Invader c s2 p b

Target + s2 p b a c* s2* p* b* a*

Docking c s2 p b c* s2* p* b* a*

+ s2 p b a

FIGS. 11A-11B, CONTINUED
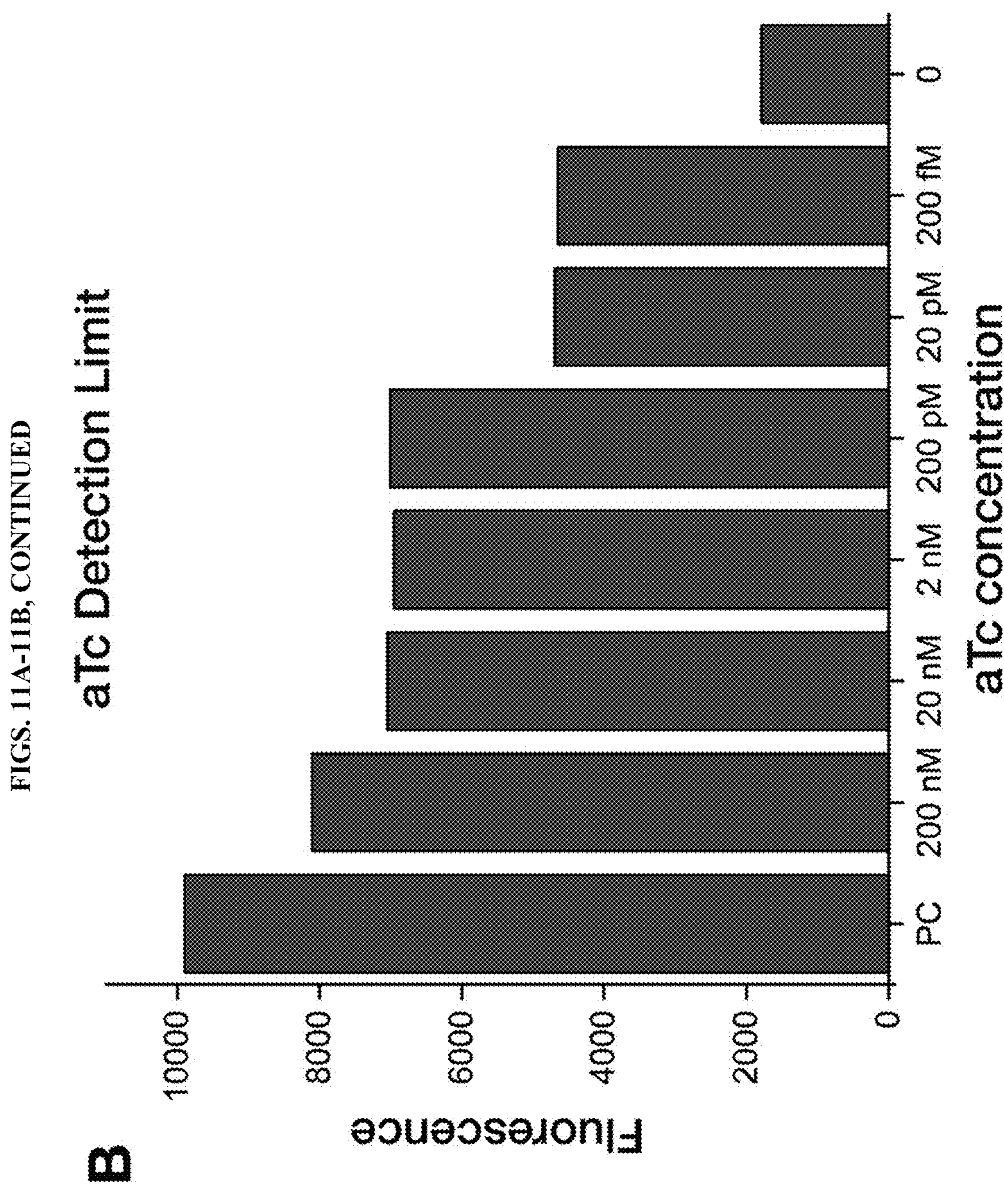

PROXIMITY-DRIVEN ACTIVATION OF CRISPR-Cas SYSTEMS FOR DETECTION OF DIVERSE MOLECULAR ANALYTES

CROSS-REFERENCE TO RELATED APPLICATIONS

This application is a national stage application filed under 35 U.S.C. § 371 of International Application No. PCT/US2020/030032, filed Apr. 27, 2020, which claims the benefit of U.S. Provisional Application Nos. 62/839,050, filed Apr. 26, 2019, and 62/976,659, filed Feb. 14, 2020, each of which is incorporated herein by reference in its entirety.

STATEMENT REGARDING FEDERALLY FUNDED RESEARCH OR DEVELOPMENT

Not applicable.

BACKGROUND

CRISPR-Cas systems function as a prokaryotic adaptive immune defense through the recognition and degradation of invading viral RNA/DNA. These systems use Clustered Regularly Interspaced Short Palindromic Repeats (CRISPR) to transcribe guide RNAs that direct Cas proteins to cleave targeted DNA and RNA. CRISPR-Cas12a systems recognize target double-stranded DNA (dsDNA) that contains a region complementary to guide RNA along with a T-rich protospacer adjacent motif (PAM). Upon recognition, Cas12a nuclease activity is initiated and a staggered dsDNA break is fashioned after the PAM site. Once activated, Cas12a also exhibits a collateral single-stranded DNase effect to cleave surrounding single-stranded DNA (ssDNA) molecules. This effect enables Cas12a to attack viral ssDNA.

Several CRISPR-Cas systems have been exploited for gene editing applications based on dsDNA cleavage capabilities that are single turnover. More recently, CRISPR-Cas systems that also display ssDNase collateral cleavage have been leveraged to develop diagnostic assays. Because this indiscriminate cleavage is multiple-turnover, these diagnostics are highly sensitive, and when coupled with an amplification reaction can reach attomolar detection limits and lower. However, the utility of CRISPR-Cas-based diagnostic tools for infections has thus far been limited to DNA/RNA detection, restricting its use to detection of infections predominately in the acute stages when viral, bacterial, fungal, and parasitic pathogens can be detected in the blood.

Standard immunoassays can detect infections even after pathogens are no longer circulating in the blood since they can exploit the prevalence of antibodies and other proteins that are generated in response to infection. These assays are typically done in a capture format where a known antigen or antibody is fixed on a surface and binding of a target macromolecule is visualized using a label, enzyme, or other reporter. Common assays include Enzyme-Linked Immunosorbent Assays (ELISA) and lateral flow assays. Because of the wide range of targets and low cost for these types of assays, they are considered standard diagnostic tools and are regularly used for detection of a range of different bacterial and viral pathogens, among others. Compared to nucleic acid tests, however, immunoassays often suffer from lower specificity, making discrimination of closely related pathogens challenging, and poorer sensitivity, since they are not as amenable to amplification as nucleic acids. To circumvent the latter limitation, several labs have tried to combine protein detection/binding with nucleic acid amplification techniques. One such example uses a small-molecule ligand and target binding event to template the formation of a DNA strand that is then amplified using polymerase chain reaction (PCR). Another example is Immuno-PCR where an ELISA assay using DNA-conjugated antibodies is coupled with PCR for highly sensitive detection (Barletta et al., *Am. J. Clin. Pathol.* 122, 20-27 (2004)). The disadvantages of such assays is that they require multiple processing steps, are limited to fluorescent readout, or require thermal cycling. These disadvantages make them unsuitable for low-cost, point-of-care assay formats. Accordingly, there remains a need in the art for rapid, inexpensive, and highly sensitive methods for detecting diverse molecular analytes such as nucleic acid complexes formed in response to antibodies, proteins, and small-molecule analytes.

SUMMARY OF THE DISCLOSURE

This disclosure is related to methods and compositions for detecting diverse molecular analytes with excellent sensitivity and specificity. As described herein, the methods and compositions are useful in a platform to detect a broader range of diseases and infections, both viral and bacterial; to enable profiling of the human immune system; and to detect impurities and toxins present in drinking water, food and beverages, and other samples.

In a first aspect, provided herein is a method of detecting a target molecule in a sample. The method can comprise or consist essentially of the steps of: (a) contacting to the sample a first synthetic nucleotide sequence comprising a first double-stranded DNA (dsDNA) spacer sequence and a first single-stranded DNA (ssDNA) that is reverse complementary to a protospacer adjacent motif (PAM) sequence, wherein the first synthetic nucleotide sequence is linked to a first antigen; and a second synthetic nucleotide sequence comprising a single-stranded sequence or a dsDNA sequence and a ssDNA PAM sequence, wherein the second synthetic nucleotide sequence is linked to a second antigen, wherein the first ssDNA and the second ssDNA PAM sequences comprise complementary sticky ends and form a double-stranded PAM (dsPAM) sequence when the first and second synthetic nucleotide sequences are brought into proximity by binding of the first and second antigens to a target molecule, and wherein the reverse complementary ssDNA PAM sequence is adjacent to the reverse complement of the spacer sequence in the first synthetic nucleotide; (b) contacting the contacted sample of (a) to: (i) a Cas nuclease that exhibits collateral ssDNase or ssRNase activity, (ii) a guide RNA (gRNA), wherein the gRNA comprises the spacer sequence, and (iii) a single-stranded DNA or RNA reporter construct; whereby, in the presence of the target molecule that binds to the first and second antigens, the gRNA forms a complex with the dsPAM sequence and the dsDNA spacer sequence and the Cas nuclease cleaves the single-stranded reporter construct; and (c) detecting cleavage of the single-stranded reporter construct, thereby detecting the presence of the target molecule in the sample.

The gRNA can be a barcoded gRNA produced by (a) contacting to a sample a first single-stranded DNA (ssDNA) sequence comprising a first gRNA barcode region and a first stem-forming region, wherein the first stem-forming region is linked to a first antigen, and a second ssDNA sequence comprising a second gRNA barcode region, a third gRNA barcode region, and a second stem-forming region having a sequence complementary to that of the first stem-forming region, wherein the second stem-forming region is linked to a second antigen, whereby, in the presence in the sample of an antibody that binds specifically to antigens of the first and second ssDNA sequences, the first and second stem-forming regions form a double-stranded DNA region; (b) contacting to the contacted sample of (a) a split DNA template that comprises (i)) a 5' phosphorylated strand having a hairpin structure that comprises a single-stranded hairpin domain sequence, a double-stranded T7 promoter sequence, and ssDNA sequences complementary to the first and second gRNA barcode regions, and (ii) a single DNA strand comprising a sequence complementary to the third gRNA barcode region, whereby, in the presence of DNA ligase and DNA polymerase, an extended double-stranded DNA sequence is obtained that comprises a double-stranded T7 promoter sequence, a double-stranded gRNA barcode region, and a double-stranded hairpin domain that encodes a conserved gRNA hairpin; and (c) contacting the extended double-stranded DNA sequence of (b) to T7 RNA polymerase, whereby a gRNA comprising first, second, and third barcodes is produced. The gRNA can be a barcoded gRNA produced by (a) contacting to a sample a first single-stranded DNA (ssDNA) sequence comprising a first gRNA barcode region and a first stem-forming region, wherein the first stem-forming region is linked to a first protein-binding probe, and a second ssDNA sequence comprising a second gRNA barcode region, a third gRNA barcode region, and a second stem-forming region having a sequence complementary to that of the first stem-forming region, wherein the second stem-forming region is linked to a second protein-binding probe, whereby, in the presence in the sample of one or more proteins that bind specifically to protein-binding probes of the first and second ssDNA sequences, the first and second stem-forming regions form a double-stranded DNA region; (b) contacting to the contacted sample of (a) a split DNA template that comprises (i) a 5' phosphorylated strand having a hairpin structure that comprises a single-stranded hairpin domain sequence, a double-stranded T7 promoter sequence, and ssDNA sequences complementary to the first and second gRNA barcode regions, and (ii) a single DNA strand comprising a sequence complementary to the third barcode region, whereby, in the presence of DNA ligase and DNA polymerase, an extended double-stranded DNA sequence is obtained that comprises a double-stranded T7 promoter sequence, a double-stranded gRNA barcode region, and a double-stranded hairpin domain that encodes a conserved gRNA hairpin; and (c) contacting the extended double-stranded DNA sequence of (b) to T7 RNA polymerase, whereby a gRNA comprising the first, second, and third barcodes is produced. The target molecule can be an antibody. The Cas nuclease can be Cas12a, Cas13a, Cas13b, Cas13d, Cas12g1, or Cas12i1. The single-stranded reporter construct can comprise a first small molecule at the 5' end and a second small molecule at the 3' end. The first and second small molecules can be selected from biotin and FAM (fluorescein). The first ssDNA and the second ssPAM sequences can comprise complementary sticky ends having a length of 5 or 6 base pairs. The first ssDNA and the second ssPAM sequences can comprise complementary sticky ends having a length of 3 to 6 base pairs.

In another aspect, provided herein is a lateral flow test device comprising or consisting essentially of (a) a plurality of single-stranded DNA (ssDNA) or single-stranded RNA (ssRNA) reporter constructs that comprise a first small molecule at the 5' end and a second small molecule at the 3' end of each ssDNA or ssRNA; (b) a Cas nuclease that exhibits collateral ssDNase or ssRNase activity; (c) a guide RNA comprising a spacer region; (d) a first synthetic nucleotide sequence comprising a first double-stranded DNA (dsDNA) spacer sequence and a first single-stranded DNA (ssDNA) that is the reverse complement of the protospacer adjacent motif (PAM) sequence, wherein the first synthetic nucleotide sequence is linked to a first antigen; and (e) a second synthetic nucleotide sequence comprising a ssDNA or dsDNA sequence and a second ssDNA PAM sequence, wherein the second synthetic nucleotide sequence is linked to a second antigen, wherein the first ssDNA and the second ssDNA PAM sequences comprise complementary sticky ends and form a double-stranded PAM (dsPAM) sequence when the first and second synthetic nucleotide sequences are brought into proximity by binding of the first and second antigens to a target molecule.

In a further aspect, provided herein is a method of detecting a target nucleic acid in a sample. The method can comprise or consist essentially of the steps of: (a) contacting to the sample a synthetic nucleotide sequence comprising a double-stranded DNA (dsDNA) spacer sequence lacking a PAM site and a first single-stranded DNA (ssDNA) toehold sequence, wherein the synthetic nucleotide sequence and target sequences are partially complementary, and wherein this interaction releases a single-stranded DNA spacer sequence; (b) contacting the contacted sample of (a) to: (i) a Cas nuclease that exhibits collateral ssDNase or ssRNase activity, (ii) a guide RNA (gRNA), wherein the gRNA comprises the reverse complement of the ssDNA spacer sequence, and (iii) a single-stranded DNA or RNA reporter construct; whereby the gRNA forms a complex with the single-stranded DNA spacer sequence and the Cas nuclease cleaves the single-stranded DNA or RNA reporter construct; and (c) detecting cleavage of the single-stranded reporter construct, thereby detecting the presence of the target nucleic acid in the sample.

In another aspect, provided herein is a method of detecting a target molecule in a sample. The method can comprise or consist essentially of the steps of: (a) contacting to the sample a first synthetic nucleotide sequence comprising a first double-stranded DNA (dsDNA) spacer sequence lacking a PAM site, a transcription-factor binding dsDNA sequence, and a first single-stranded DNA (ssDNA) toehold sequence, wherein the dsDNA is bound to a transcription factor that recognizes the target molecule; and a second synthetic nucleotide sequence comprising a single-stranded invader DNA sequence, wherein the first and second synthetic sequences are partially complementary and interact when the transcription factor recognizes the target molecule and releases the first synthetic nucleotide sequence, and wherein this interaction exposes a single-stranded DNA (ssDNA) spacer sequence; (b) contacting the contacted sample of (a) to: (i) a Cas nuclease that exhibits collateral ssDNase or ssRNase activity, (ii) a guide RNA (gRNA), wherein the gRNA comprises the reverse complement of the ssDNA spacer sequence, and (iii) a single-stranded DNA or RNA reporter construct; whereby the gRNA forms a complex with the ssDNA spacer sequence and the Cas nuclease cleaves the single-stranded reporter construct; and (c) detecting cleavage of the single-stranded reporter construct, thereby detecting the presence of the target molecule in the sample.

In a further aspect, provided herein is a method of detecting a target molecule in a sample. The method can comprise or consist essentially of (a) contacting to the sample a first synthetic nucleotide sequence comprising a first double-stranded DNA (dsDNA) target sequence lacking a PAM site and a first single-stranded DNA (ssDNA) toehold sequence, wherein the first synthetic nucleotide sequence is linked to a first antigen; and a second synthetic nucleotide sequence comprising a single-stranded invader DNA sequence, wherein the second synthetic nucleotide sequence is linked to a second antigen, wherein the first and second sequences are partially complementary and interact when brought into proximity by binding of the first and second antigens to a target molecule, and wherein this interaction exposes a single-stranded DNA spacer sequence; (b) contacting the contacted sample of (a) to: (i) a Cas nuclease that exhibits collateral ssDNase or ssRNase activity, (ii) a guide RNA (gRNA), wherein the gRNA comprises the reverse complement of the ssDNA spacer sequence, and (iii) a single-stranded DNA or RNA reporter construct; whereby, in the presence of the target molecule that binds to the first and second antigens, the gRNA forms a complex with the ssDNA spacer sequence and the Cas nuclease cleaves the single-stranded reporter construct; and (c) detecting cleavage of the single-stranded reporter construct, thereby detecting the presence of the target molecule in the sample. The target molecule can be an antibody. The Cas nuclease can be Cas12a, Cas13a, Cas13b, Cas13d, Cas12g1, or Cas12i1. The single-stranded reporter construct can comprise a first small molecule at the 5' end and a second small molecule at the 3' end. The first and second small molecules can be selected from biotin and FAM (fluorescein). The toehold sequence in the first synthetic nucleotide sequence can have a length of 1 to 15 nucleotides.

In another aspect, provided herein is a lateral flow test device for detecting a target nucleic acid, the device comprising or consisting essentially of (a) a plurality of single-stranded DNA (ssDNA) or single-stranded RNA (ssRNA) reporter constructs, each of which comprises a first small molecule at its 5' end and a second small molecule at its 3' end; (b) a Cas nuclease that exhibits collateral ssDNase or ssRNase activity; (c) a guide RNA comprising a sequence complementary to a ssDNA target sequence; (d) a synthetic nucleotide sequence comprising a first double-stranded DNA (dsDNA) target sequence lacking a PAM site and a single-stranded DNA (ssDNA) toehold sequence, wherein the first dsDNA target sequence is released upon interaction with the target nucleic acid to be detected.

In another aspect, provided herein is a lateral flow test device detecting a target molecule, the device comprising or consisting essentially of (a) a plurality of single-stranded DNA (ssDNA) or single-stranded RNA (ssRNA) reporter constructs, each of which comprises a first small molecule at its 5' end and a second small molecule at its 3' end; (b) a Cas nuclease that exhibits collateral ssDNase or ssRNase activity; (c) a guide RNA comprising a sequence complementary to a ssDNA target sequence; (d) a first synthetic nucleotide sequence comprising a first double-stranded DNA (dsDNA) target sequence lacking a PAM site, a transcription factor-binding dsDNA sequence and a single-stranded DNA (ssDNA) toehold sequence; (e) a transcription factor that binds to the binding site on the first synthetic nucleotide and that can recognize a target molecule; and (f) a second synthetic nucleotide sequence comprising a single-stranded invader sequence partially complementary to the first synthetic nucleotide sequence, wherein the first and second synthetic nucleotide sequences interact when the transcription factor binds to the target molecule and releases the first synthetic nucleotide sequence.

In a further aspect, provided herein is a lateral flow test device comprising or consisting essentially of (a) a plurality of single-stranded DNA (ssDNA) or single-stranded RNA (ssRNA) reporter constructs that comprise a first small molecule at the 5' end and a second small molecule at the 3' end of each ssDNA or ssRNA; (b) a Cas nuclease that exhibits collateral ssDNase or ssRNase activity; (c) a first synthetic nucleotide sequence comprising a first double-stranded DNA (dsDNA) spacer sequence lacking a PAM site and a single-stranded DNA (ssDNA) toehold sequence, wherein the first synthetic nucleotide sequence is linked to a first antigen; and (d) a second synthetic nucleotide sequence comprising an invader sequence partially complementary to the first synthetic nucleotide sequence, wherein the second synthetic nucleotide sequence is linked to a second antigen, wherein the first and second synthetic nucleotide sequences are brought into proximity by binding of the first and second antigens to a target molecule.

In another aspect, provided herein is a kit comprising a lateral test flow device of this disclosure.

BRIEF DESCRIPTION OF THE DRAWINGS

FIG. 2 is a schematic illustrating protein-driven CRISPR-Cas activation. A) Production of a deactivated Cas12a dsDNA substrate from an active dsDNA substrate. B) (Step 1) Two DNA-antigen strands containing short sticky ends containing the PAM site are used for protein recognition. (Step 2) DNA-antigens bind to target antibodies, co-localizing the strands. The induced proximity of the two DNA-antigen strands enables their sticky ends to hybridize, forming a suitable target DNA substrate for cas12a. (Step 3) The Cas12a/guide RNA complex is activated and begins collateral cleavage of ssDNA reporter strands.

FIG. 3A is a schematic illustrating formation of guide RNAs based on antibody-driven DNA ligation. Antigen-conjugated DNA strands bind to the antibody analyte promoting w-w* hybridization. Split DNA template strands then bind to the assembled DNA complex and a ligase is used to join the two DNA template strands. Addition of DNA polymerase extends the DNA template and displaces it from the DNA complex. The extended product is transcribed to produce an activated CRISPR guide RNA. As described herein, domain H* will ultimately be used to encode the conserved guide RNA hairpin following ligation and transcription by T7 RNA polymerase (T7 RNAP).

DETAILED DESCRIPTION

Figure 1:
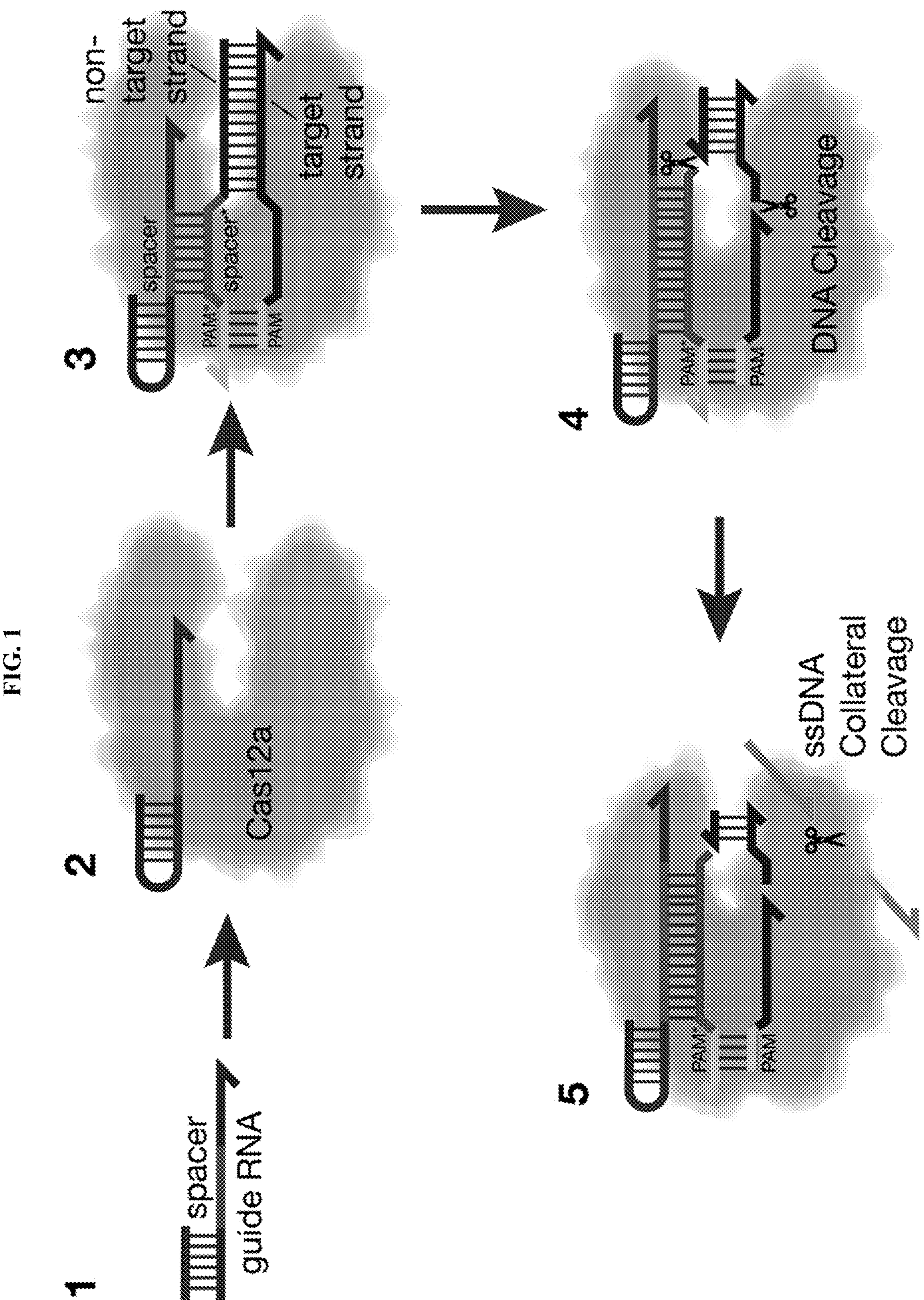
FIG. 1 is a schematic illustrating an exemplary CRISPR-Cas12a mechanism. (Step 1) The guide RNA sequence contains a conserved hairpin sequence and the sequence of the target DNA spacer. (Step 2) Guide RNA interacts with the Cas12a protein to form a Cas12a/guide RNA complex. (Step 3) Cas12a/guide RNA complex recognizes and binds to the target DNA and PAM site based on the spacer sequence specified by the guide RNA. This activates the Cas12a protein. (Step 4) The Cas protein cleaves the double-stranded DNA. (Step 5) Once activated, Cas also cleaves single-stranded DNA nonspecifically through a collateral cleavage effect.

All publications, including but not limited to patents and patent applications, cited in this specification are herein incorporated by reference as though set forth in their entirety in the present application.

The methods and compositions provided herein are based at least in part on the inventors' development of a rapid, highly sensitive assay for detecting molecular analytes such as antibodies and proteins using a protein-driven nucleic acid assembly to activate CRISPR-Cas nucleases. Also provided herein are uses of the sensitive analyte detection methods in a generalizable analyte detection platform and in convenient low-cost diagnostic assays for point-of-care use. Advantages of the methods and compositions provided herein are multifold. For example, the highly sensitive protein detection methods provided herein do not require sophisticated instrumentation and provide results that can be interpreted through convenient, low-cost lateral flow assay formats. Moreover, these methods can be implemented in multiplexed reactions to enable detection of multiple proteins at the same time. This capability can be exploited to enable panel-based tests for multiple pathogens or to improve assay specificity. The methods described herein employ CRISPR-Cas to detect nucleic acid complexes formed in response to antibodies, proteins, and small-molecule analytes. Use of CRISPR-Cas systems yields improvements to detection sensitivity, without requiring thermal cycling or additional processing steps. Such strategies extend the CRISPR-Cas response to proteins and antibodies will allow for the design of powerful diagnostics to detect a broader range of diseases and infections, both viral and bacterial, and enable profiling of the human immune system.

Accordingly, in a first aspect, provided herein is a method to detect diverse molecular analytes with excellent sensitivity using convenient isothermal reactions. The general strategy described herein employs two analyte recognition molecules (e.g., antibody, protein, epitope, or small molecule) that are used to bind to the molecular analyte of interest. The two analyte recognition molecules are also conjugated to one or more nucleic acids (e.g., DNA, RNA). In the presence of the molecular analyte, the recognition molecules are brought into close proximity, in turn co-localizing their respective nucleic acids. This effect promotes a hybridization reaction between the nearby nucleic acids, which are ultimately recognized by a CRISPR-Cas enzyme. Recognition activates the collateral ssDNase or ssRNase activity of the CRISPR-Cas enzyme and is used to report on the presence of the molecular analyte of interest. This method can be broadly applied for any molecule that can bind to a recognition molecule that is conjugated to a nucleic acid. Thus, it can be used to detect molecular analytes such as diverse antibodies, proteins, small molecules, carbohydrates, lipids, and even combinations of analytes that bind to one another. The reactions can take place in vitro, in paper-based systems, and in living or fixed cells.

In another aspect, recognition of the molecular analytes involves a transcription factor that in the absence of the analyte binds to a partial dsDNA sequence. In the presence of the analyte, the transcription factor recognizes the analyte and releases the partial dsDNA sequence and enables the partial dsDNA sequence to interact with an invading ssDNA sequence to expose an activating ssDNA sequence that is recognized by a CRISPR-Cas enzyme. Recognition activates the collateral ssDNase or ssRNase activity of the CRISPR-Cas enzyme and is used to report on the presence of the molecular analyte of interest. This method can be broadly applied for any molecule that can be recognized by a transcription factor of which there are many naturally occurring and synthetic examples. The reactions can take place in vitro, in paper-based systems, and in living or fixed cells.

The subsequent sections provide details for three specific examples: (1) detection of an antibody via peptide-DNA conjugates and a conditional CRISPR-Cas dsDNA target substrate, (2) multiplexed detection of different antibodies using barcoded peptide-DNA conjugates and proximity-driven ligation of a guide RNA transcription template, and (3) detection of small molecules via transcription factors and a conditional CRISPR-Cas ssDNA target substrate. These examples describe experiments conducted using the Cas12a (also known as Cpf1) CRISPR enzyme. It should be understood that similar systems can be implemented using other CRISPR enzymes that exhibit collateral ssDNase or ssRNase activity or are capable of multiple-turnover RNA or DNA cleavage reactions. For example, CRISPR enzymes that exhibit collateral ssDNase or ssRNase activity include, without limitation, Cas12a, Cas13a, Cas13b, Cas13d, Cas12g1, and Cas12i1.

Analyte Detection Via Conditional CRISPR-Cas Target Substrates

Generally, once assembled into a complex with a guide RNA, Cas12a will activate its collateral cleavage activity upon recognition of a dsDNA sequence containing the spacer sequence adjacent to the T-rich PAM site (see FIG. 1, Step 3). The spacer sequence for targeting is specified by the guide RNA, and recognition occurs when the RNA hybridizes to the non-target strand of the dsDNA. Alternatively, Cas12a is activated by a ssDNA that contains the reverse complement of the spacer sequence. In this case, the ssDNA substrate carries out a similar function to the non-target strand of the dsDNA case, with the guide RNA directly hybridizing to the sequence complementary to the spacer. Recognition of ssDNA by Cas12a has no sequence constraints related to the PAM sequence or its reverse complement PAM*. The molecular detection methods described herein integrate these different behaviors of CRISPR enzymes like Cas12a in recognizing dsDNA and ssDNA to generate a conditional target DNA substrate.

For the methods and compositions provided herein, we started with an ideal target dsDNA substrate for Cas12a (FIG. 2A, top). This substrate consisted of a dsDNA with a spacer sequence and PAM site flanked by dsDNA regions on either end. We then cleaved the target strand at the location in between the PAM and the spacer sequence, and we cleaved the non-target strand at a site to the 3' end of PAM* (FIG. 2A, bottom). This operation served four main purposes. First, it deactivated the dsDNA target by splitting the system into two dsDNAs and separating the PAM site from the spacer sequence. Second, it prevented any ssDNA substrate activity by keeping the spacer region and the neighboring flanking region double stranded, thus preventing direct hybridization with the Cas12a/guide RNA complex. Third, it created a pair of complementary sticky ends containing the PAM site and with overlap lengths determined by the cleavage site in the non-target strand. Through careful engineering of the sticky end length and sequence, it is possible to prevent spontaneous hybridization of the two target DNA substrate halves unless another molecular cue brings them into close proximity. Lastly, we determined that Cas12a can tolerate nicks between the PAM site and the spacer in the target strand and nicks downstream of the PAM* site in the non-target strand. Thus, hybridization of the two halves assembles an active Cas12a dsDNA target substrate.

The Cas12a DNA target substrate was integrated into an antibody detection scheme as shown in FIG. 2B. The two halves of the substrate are each conjugated to a peptide antigen that is specific to the antibody being detected. Possible antigens depend on the analyte of interest and include small molecules, proteins, peptides, nanobodies, aptamers, and other biomolecules. A linker sequence is used between the conjugation site and the DNA target halves to span a distance tailored to the geometry of the specific antigen-analyte combination. Typically, this linker can vary in length from 5-50 bases and consists of a poly-nucleotide repeat sequence (e.g., poly-T, poly-A, poly-G, poly-C), or any non-self-complementary sequence that will also not interact with templated nucleotides.

In general, the overlap length can vary depending on the target molecule to be detected (i.e., antibody, protein, viral capsid protein, small molecule, etc.), the overlap sequence, the reaction buffer, and the degree of complementarity between overhangs. In most cases, it will range from 1 to 10 nucleotides in length and non-complementary spacer sequences can be appended to the 3' ends of one or both of the sticky ends to reduce base stacking effects. Preferably, the overhang length is 5 or 6 bases of overlap, but this length can vary based on the target molecule to be detected. In the absence of the target molecule at the optimal 5 to 6 base overlap, these single-stranded overhangs are short enough to prevent spontaneous hybridization in solution, ensuring that the Cas nuclease that exhibits collateral ssDNase or ssRNase activity (e.g., Cas12a, Cas13a, Cas13b, Cas13d, Cas12g1, Cas12i1) remains in an inactive state. In the presence of an antibody biomarker (for example), the two antigen-DNA conjugates bind to the antibody, bringing the single-stranded protospacer adjacent motif (PAM) sites into close proximity and promoting their hybridization (FIG. 2B). Hybridization of the target DNA halves activates the substrate and enables the Cas12a/guide RNA complex to begin its aggressive collateral ssDNase activity, which is trained against ssDNA reporter strands (FIG. 2C). The ssDNase activity of Cas12a permits detection of the analyte using the status of the ssDNA reporter strands as described below. In this manner, the assembly of components necessary for CRISPR-Cas activation is conditional on the presence or absence of the target molecule. This assay can also be applied to the detection of a variety of other analytes simply by conjugating the DNA sequences to antigens specific for the analyte of interest.

As used herein, a "guide RNA" (gRNA) is nucleotide sequence that is complementary to at least a portion of a target gene. In some embodiments, the sequence of PAM is dependent upon the species of Cas nuclease used in the architecture. It should be noted that the DNA-targeting sequence may or may not be 100% complementary to the target polynucleotide (e.g., gene) sequence. Examples of PAM sequences (also referred to herein as "PAM sites") are known (see, e.g., Shah et al., *RNA Biology* 10 (5): 891-899, 2013).

In some cases, the method comprises the steps of: (a) contacting to the sample a first synthetic nucleotide sequence comprising a first double-stranded DNA (dsDNA) target sequence and a first single-stranded DNA (ssDNA) PAM sequence, wherein the first synthetic nucleotide sequence is linked to a first antigen; and a second synthetic nucleotide sequence comprising a dsDNA spacer sequence, a second dsDNA target sequence, and a first ssDNA PAM sequence, wherein the second synthetic nucleotide sequence is linked to a second antigen. The first and second ssDNA PAM sequences can comprise complementary sticky ends and form a double-stranded PAM (dsPAM) sequence when the first and second synthetic nucleotide sequences are brought into proximity by binding of the first and second antigens to a target molecule. In some cases, the first and second ssPAM sequences comprise complementary sticky ends having a length of 3 to 6 base pairs. In some cases, the second ssDNA PAM sequence is 5' to the dsDNA spacer sequence of the second synthetic nucleotide sequence.

A "target site" or "target sequence" refers to a nucleic acid sequence that defines a portion of a nucleic acid to which a binding molecule may specifically bind under conditions sufficient for binding to occur.

As used herein, the terms "synthetic" and "engineered" are used interchangeably and refer to a non-naturally occurring nucleic acid molecule that has been created or modified by the hand of man (e.g., using recombinant DNA technology) or is derived from such a molecule (e.g., by transcription, translation, etc.). A nucleic acid molecule may be similar in sequence to a naturally occurring nucleic acid but typically contains at least one artificially created insertion, deletion, inversion, or substitution relative to the sequence found in its naturally occurring counterpart. Likewise, a cell that contains a synthetic or engineered nucleic acid is considered to be an engineered cell.

In another step, the method further comprises (b) contacting the contacted sample of (a) to: (i) a Cas nuclease that exhibits collateral ssDNase or ssRNase activity, (ii) a guide RNA (gRNA), wherein the gRNA comprises the reverse complement of the dsDNA spacer sequence and binds to the dsPAM sequence, and (iii) a single-stranded reporter construct. In the presence of the target molecule that binds to the first and second antigens, the gRNA forms a complex with the dsPAM sequence and the Cas nuclease cleaves the single-stranded reporter construct. The method further comprises (c) detecting cleavage of the single-stranded reporter construct, thereby detecting the presence of the target molecule in the sample.

Figures 5A, 5B:
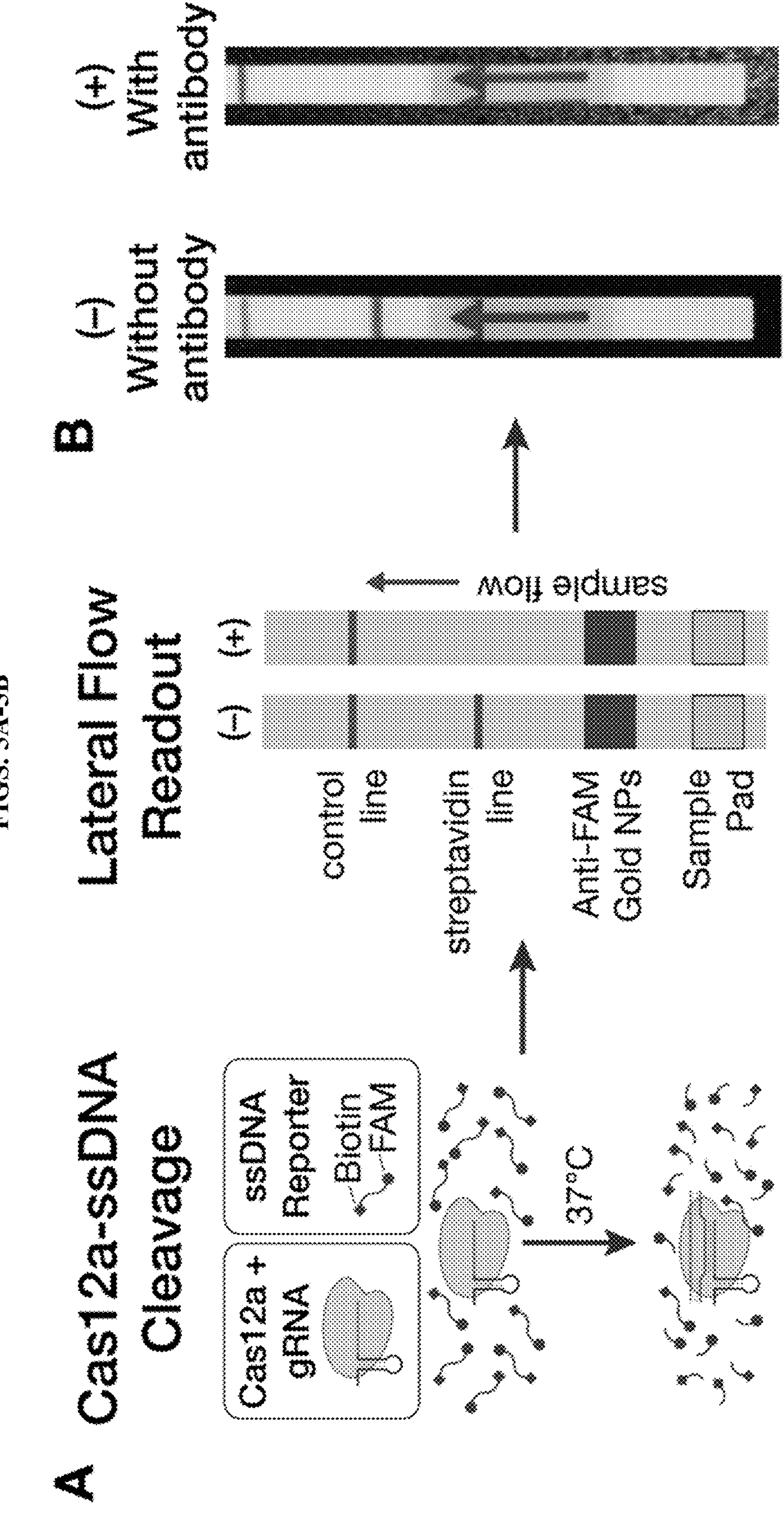
FIGS. 5A-5B demonstrate lateral flow assay readout. A) Upon recognition of target DNA, Cas12a is activated and begins to cleave reporter ssDNA. This ssDNA has biotin and FAM modifications at the 5' and 3' ends to interact with the lateral flow assay. An intact reporter strand results in two bands as shown on the lateral flow assay. Cleavage of reporter results in one band. B) Experimental results demonstrate that the 6-bp overhang design shows two bands with no antibody present and one band with the antibody present. This indicated antibody-positive sample had ssDNase cleaved reporter strands.

In some cases, the single-stranded reporter construct comprises a first small molecule at the 5' end and a second small molecule at the 3' end. As illustrated in FIGS. 2B and 5A, the first and second small molecules can be selected from biotin and FAM (fluorescein). Other detectable molecules that may be used according to the methods provided herein include, without limitation, digoxigenin, enzymatic reporters (e.g., β-galactosidase, alkaline phosphatase, DHFR, CAT), fluorescent or chemiluminescent reporters (e.g., GFP variants, mCherry, luciferase, e.g., luciferase derived from the firefly (*Photinus pyralis*) or the sea pansy (*Renilla reniformis*) and mutants thereof), etc. The presence or absence of the single-stranded reporter construct can also be detected using nucleic acid sensors, such as a toehold switch, loop-mediated riboregulator, three-way junction (3WJ) repressor, single-nucleotide-specific programmable riboregulator (SNIPR), toehold repressor, etc., to produce a protein reporter signal that can be detected in cell-free transcription-translation reactions. Potential reporter signals include enzymatic reporters (e.g., β-galactosidase, alkaline phosphatase, DHFR, CAT), and fluorescent or chemiluminescent reporters (e.g., GFP variants, mCherry, luciferase, e.g., luciferase derived from the firefly (*Photinus pyralis*) or the sea pansy (*Renilla reniformis*) and mutants thereof), etc.

When the single-stranded reporter construct comprises biotin and fluorescein, nanoparticles comprising anti-FAM antibodies can be used to detect the cleavage event. For example, the assay can take place on a lateral flow device configured such that the Cas-ssDNA cleavage reaction occurs on a sample pad at one end of a lateral flow strip. Without the antibody (no activation), intact reporter ssDNAs are captured by the biotin line and in turn capture the nanoparticles via the anti-FAM antibodies. Thus, inactivated Cas12a reactions will yield both a sample (streptavidin) line and a control line in the lateral flow strip. Referring to FIG. 5, differences in band formation are detectable with two bands for antibody-negative sample and one band for the antibody-positive sample as expected. Upon recognition of a target molecule in a sample contacted to the lateral flow, the gRNA/Cas-nuclease complex is activated. Activation of Cas12a cleavage of the ssDNA reporters results in the formation of only a single band. In other words, activated Cas12a reactions (a "positive" result for presence of a target molecule in the sample) will yield a control line in the lateral flow strip but no streptavidin sample line.

Multiplexable Analyte Detection using Proximity-Driven Guide RNA Synthesis

Beyond the dsDNA substrate, other vital components required for CRISPR-Cas activation can be assembled conditionally for the purposes of analyte detection. For example, the second approach employs proximity-driven ligation to generate barcoded guide RNAs for multiplexed analyte detection. For demonstration purposes, this method is described for the detection of antibody and protein analytes. However, it should be understood that it can be applied to diverse analytes, including carbohydrates, lipids, small molecules, combinations thereof, and combinations of analytes in close proximity, depending on the analyte recognition molecule used.

For antibody detection, antigens to which the antibody specifically binds are conjugated to two DNA strands as shown in FIG. 3A. The two strands contain the sequences S1, S2, and S3, which will subsequently be used for guide RNA barcoding, along with short complementary domains w and w*, which perform a similar function as the sticky ends in the conditional target dsDNA substrate (described above). The w/w* domains are designed to be sufficiently short to ensure that the two strands will not hybridize when free in solution. After addition of the antibody analyte, the two antigen-DNA conjugates bind to the antibody and are brought into close proximity. Here, these strands hybridize to generate a small stem region w-w*, bringing the single-stranded barcoding regions (i.e., domains S1, S2, and S3) together to form a long single-stranded DNA region. This region is in turn used as a splinting site for ligation of a split DNA template. As shown in FIG. 3A, the split DNA template consists of (1) a 5' phosphorylated strand with a hairpin structure that contains a double-strand T7 promoter sequence along with the single-stranded domains H*, S1, and S2*, and (2) a strand with the sequence S3*. The domain H* will ultimately be used to encode the conserved guide RNA hairpin following ligation and transcription by T7 RNA polymerase (T7 RNAP). The split DNA template strands are used to bind to the splinting site, and DNA ligase is used to join the two strands into a single template molecule. DNA polymerase then extends the single template molecule, which in turn releases it from the antibody-DNA complex. The antibody-DNA complex can again serve as a splinting site for the split DNA template, thus providing signal amplification. The T7 RNAP promoter site in the extended DNA template is then used to transcribe multiple copies of the output guide RNA, yielding additional amplification. Ultimately, the transcribed guide RNA forms a complex with Cas12a and its activation can be monitored through the cleavage of reporter ssDNAs. Importantly, the Cas12a/guide RNA complex will only activate in reactions where a dsDNA having a spacer matching the guide RNA is present.

Figure 3B:
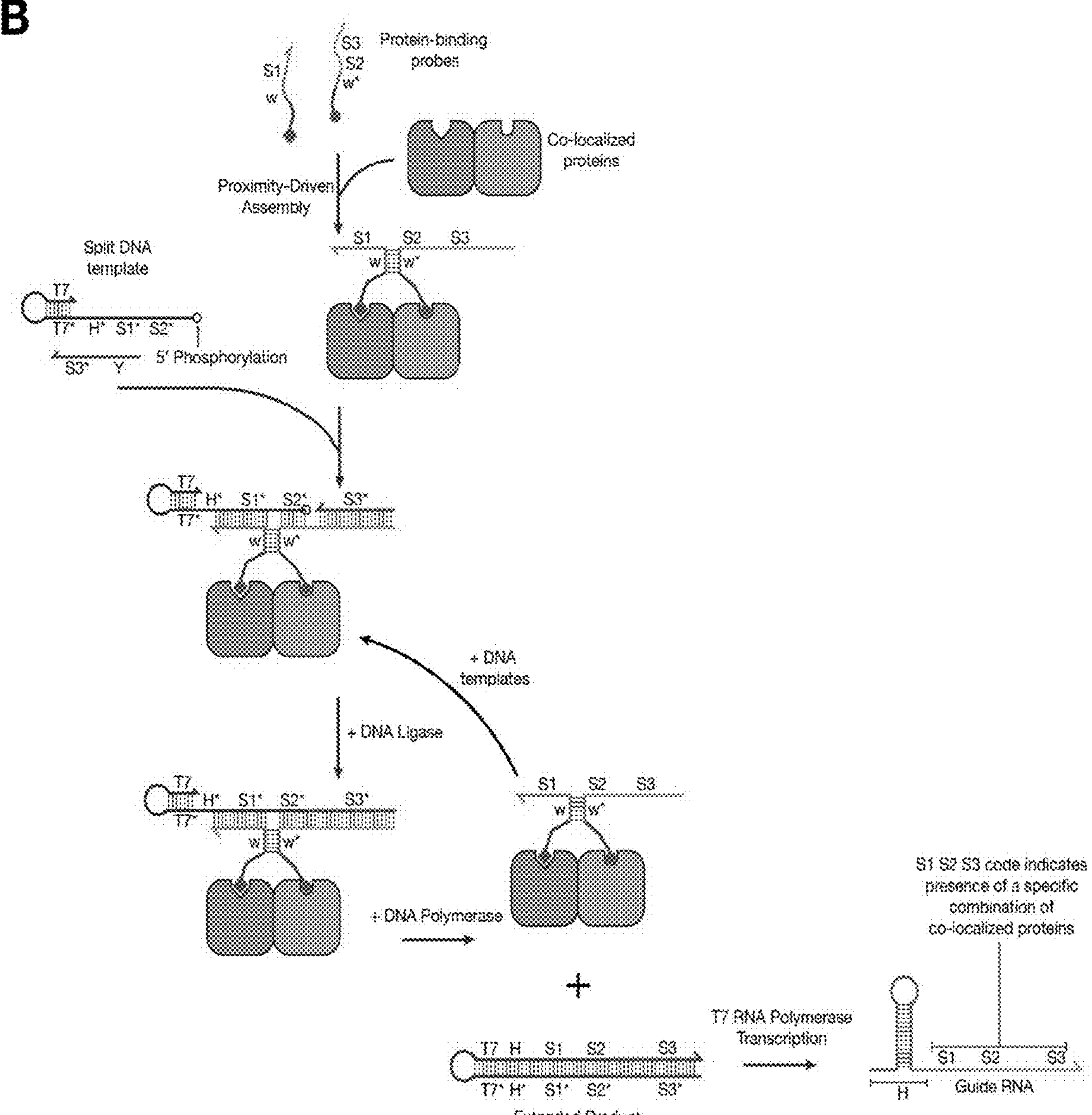
FIG. 3B is a schematic illustrating formation of guide RNAs based on protein-driven DNA ligation. Antigen-conjugated DNA strands bind to interacting protein analytes promoting w-w* hybridization. Split DNA template strands then bind to the assembled DNA complex and a ligase is used to join the two DNA template strands. Addition of DNA polymerase extends the DNA template and displaces it from the DNA complex. The extended product is transcribed to produce an activated CRISPR guide RNA.
Figure 3C:
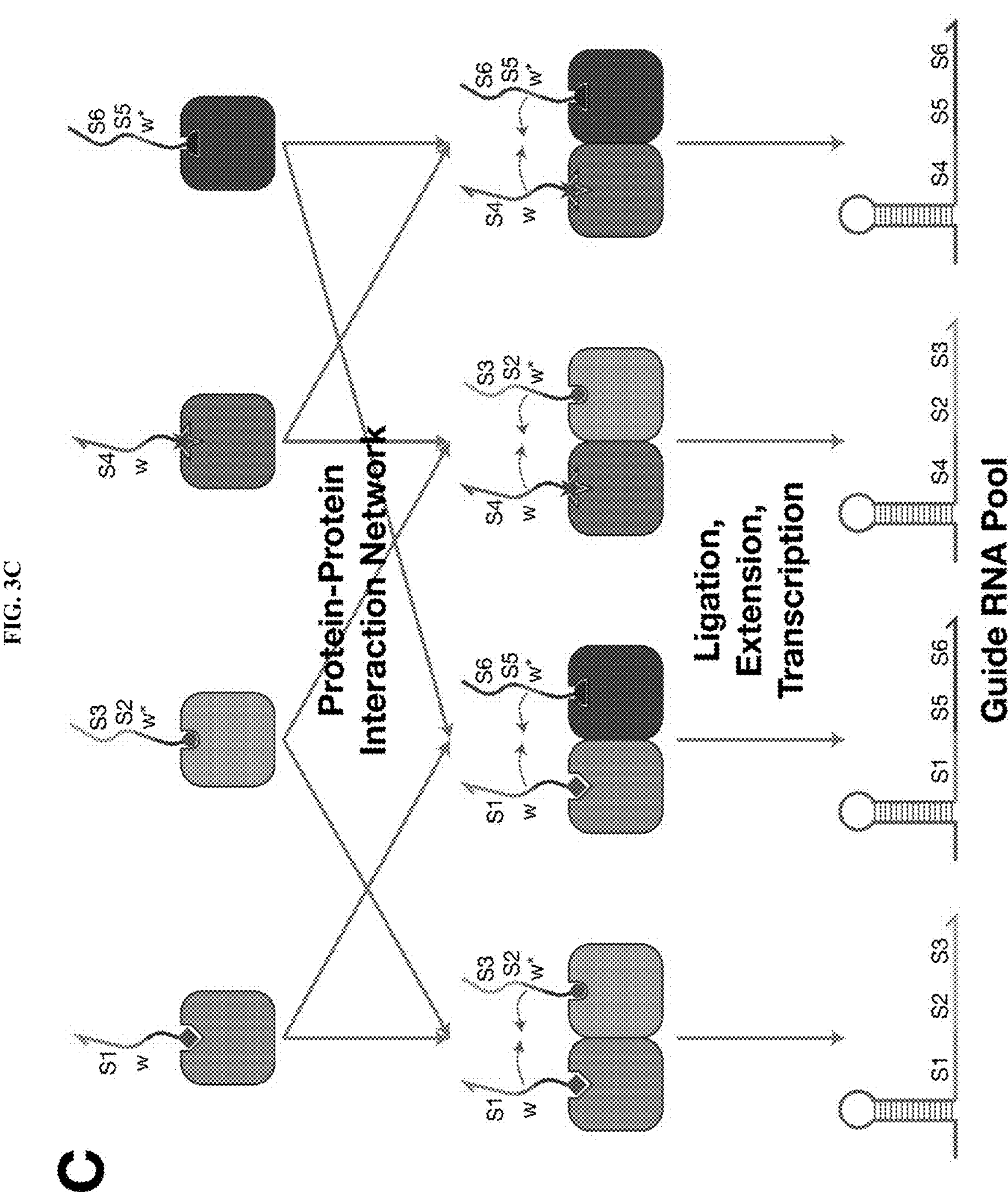
FIG. 3C illustrates the recording of protein-protein interaction networks using protein-driven DNA ligation and guide RNA formation. Antigen-conjugated DNA strands with different barcode fragments bind to their corresponding target proteins. Protein-protein interactions bring the two DNA barcode fragments into close proximity and enable ligation followed by primer extension. Transcription of the resulting extended DNA templates leads to a pool of guide RNAs defined by the set of observed protein-protein interactions.

To enable multiplexed detection of different analytes, antigen-DNA conjugates can be prepared with unique sequences to generate guide RNAs with barcoded spacers. For example, modules S1, S2, and S3 can form one strand or modules S4, S5, and S6 can form another after ligation to two different antibodies. In addition, the proximity-driven system can be employed to detect any different analytes, such as cell-surface proteins or viral capsid proteins, provided that the analytes are nearby one another (FIG. 3B). For protein detection, antibodies or nanobodies are conjugated to unique DNA sequences, each with a particular barcode sequence fragment that will be incorporated into the guide RNA spacer. When two proteins bind to one another or are in close proximity, the bound DNA strands will hybridize through the w-w* interaction. This event will enable ligation of the split DNA templates, primer extension, and finally guide RNA transcription. Since each protein analyte can be assigned a different barcode sequence fragment for incorporation into the spacer, it is possible to use the proximity-driven ligation to record a large set of different protein-protein interactions, with each interaction assigned a unique barcode (FIG. 3C). The resulting pool of guide RNA templates can then be transcribed and analyzed through the activated Cas12a collateral ssDNase activity.

This guide-RNA-enabled detection method offers two additional benefits to the first method. First, it integrates two additional layers of signal amplification beyond the Cas12a collateral cleavage activity. The first layer of amplification occurs through the release of the DNA template through primer extension, which enables the antigen-DNA conjugates to template repeated ligation reactions. The second layer of amplification occurs through transcription of the guide RNA itself. Each guide RNA can complex with a Cas12a enzyme for additional collateral cleavage activity. Second, it enables multiplexed detection of different analytes or combinations thereof with modular guide RNA barcode fragments. Ligation methods have previously been used to amplify protein-based signals by forming complete strands that then react with a downstream reaction for amplification; however, these approaches are not as amenable to implementation in point-of-care settings and do not provide the same multiplexing capacity afforded by CRISPR cleavage specificity.

The multiplexing capabilities of this system is particularly well-suited for answering fundamental questions in cell biology in convenient assays and for identifying different pathogens. As an example of the latter, multiplexing via barcoded guide RNAs can be used to target the different types of neuraminidase (N) and hemagglutinin (HA) proteins expressed on the surface of influenza virus capsids. For each strain of influenza, there are various types of N and HA proteins. The combination of these proteins are used to identify the strain of flu each year, such as H1N1 or H5N1. Using specific modular combinations for each type of N and HA protein, different template strands can be formed upon binding, resulting in a method to rapidly identify flu types. This modular ligation process coupled with CRISPR-Cas activation and collateral cleavage of a reporter can be used to detect a wide range of targets in a single system, broadening potential application.

In some cases, a barcoded gRNA is produced by (a) contacting to a sample a first single-stranded DNA (ssDNA) sequence comprising a first gRNA barcode region and a first stem-forming region, wherein the first stem-forming region is linked to a first antigen, and a second ssDNA sequence comprising a second gRNA barcode region and a second stem-forming region having a sequence complementary to that of the first stem-forming region, wherein the second stem-forming region is linked to a second antigen, whereby, in the presence in the sample of an antibody that binds specifically to antigens of the first and second ssDNA sequences, the first and second stem-forming regions form a double-stranded DNA region. The method of producing a barcoded gRNA further comprises (b) contacting to the contacted sample of (a) a split DNA template that comprises (i) a 5' phosphorylated strand having a hairpin structure that comprises a single-stranded hairpin domain sequence, a double-stranded T7 promoter sequence, and ssDNA sequences complementary to the first and second gRNA barcodes, and (ii) a single DNA strand comprising a third barcode sequence, whereby, in the presence of DNA ligase and DNA polymerase, an extended double-stranded DNA sequence is obtained that comprises a double-stranded T7 promoter sequence, a double-stranded gRNA barcode region, and a double-stranded hairpin domain that encodes a conserved gRNA hairpin. The method further comprises contacting the extended double-stranded DNA sequence of (b) to T7 RNA polymerase, whereby a gRNA comprising the first, second, and third barcodes is produced.

As used herein, the term "hairpin" or "hairpin structure" refers to an intramolecular structure of a nucleic acid sequence at the chosen assay temperature mediated by hybridization of complementary sequences at the 5'- and the 3'-end of the nucleic acid sequence.

In some cases, a barcoded gRNA is produced by the following steps: (a) contacting to a sample a first single-stranded DNA (ssDNA) sequence comprising a first gRNA barcode region and a first stem-forming region, wherein the first stem-forming region is linked to a first protein-binding probe, and a second ssDNA sequence comprising a second gRNA barcode region, a third gRNA barcode region, and a second stem-forming region having a sequence complementary to that of the first stem-forming region, wherein the second stem-forming region is linked to a second protein-binding probe. In the presence in the sample of one or more proteins that bind specifically to protein-binding probes of the first and second ssDNA sequences, the first and second stem-forming regions form a double-stranded DNA region.

In the next step, the contacted sample of (a) is contacted to a split DNA template that comprises (i) a 5' phosphorylated strand having a hairpin structure that comprises a single-stranded hairpin domain sequence, a double-stranded T7 promoter sequence, and ssDNA sequences complementary to the first and second gRNA barcodes, and (ii) a single DNA strand comprising a third barcode sequence. In the presence of DNA ligase and DNA polymerase, an extended double-stranded DNA sequence is obtained that comprises a double-stranded T7 promoter sequence, a double-stranded gRNA barcode region, and a double-stranded hairpin domain that encodes a conserved gRNA hairpin.

In the next step, the extended double-stranded DNA sequence of (b) is contacted to T7 RNA polymerase, whereby a gRNA comprising the first, second, and third barcodes is produced.

Experimental Validation: CRISPR-Cas activity following activation of conditional target dsDNA substrates or guide RNA template ligation is observed through the collateral cleavage of a single stranded reporter with modification suitable for detection. We employ two methods for detecting this effect: fluorescence where kinetic rates can be readily monitored, and a paper-based format using lateral flow assays.

Figure 4A:
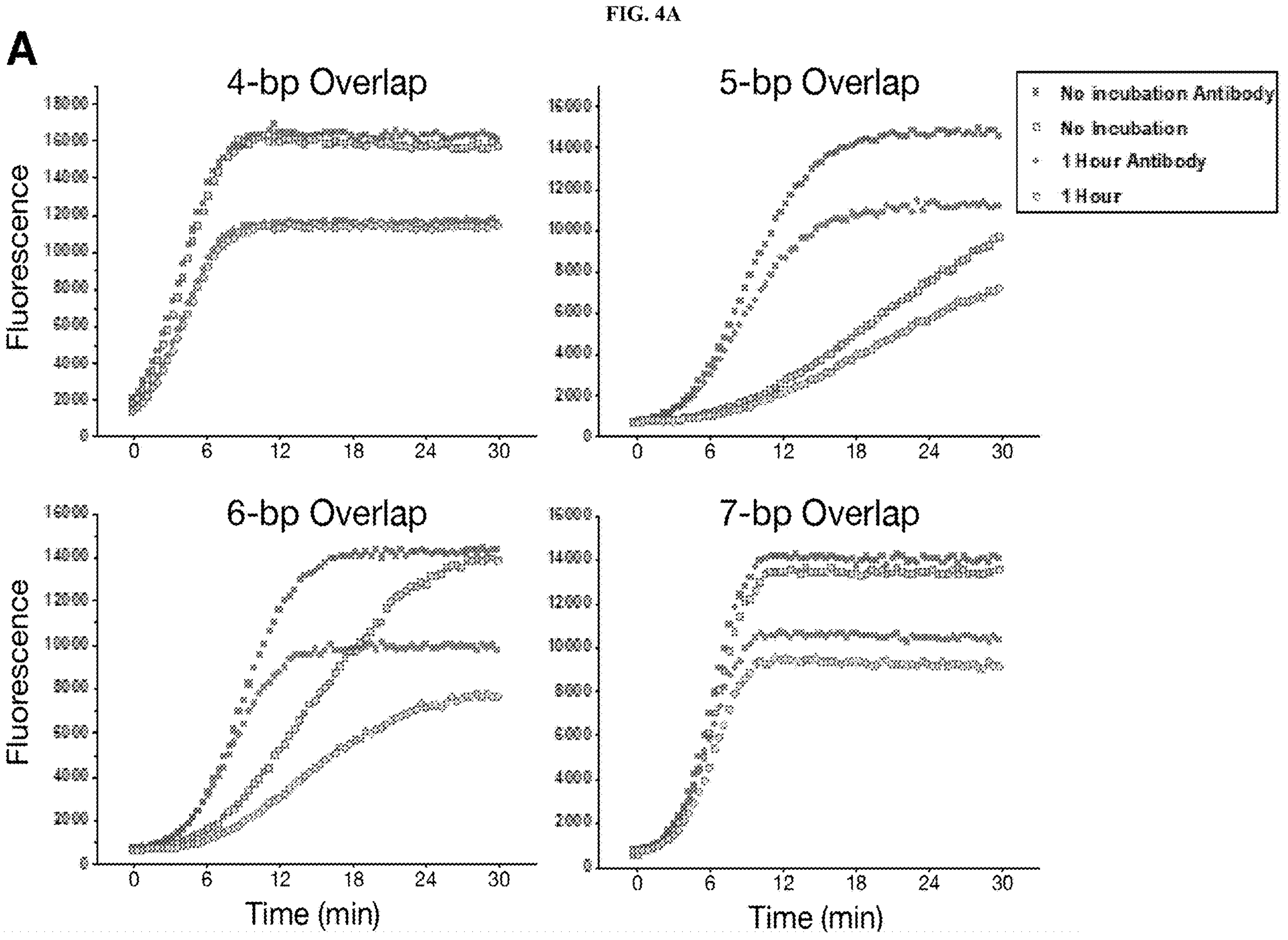
FIGS. 4A-4B demonstrate fluorescence readout of CRISPR-Cas activation. A) Sticky end overhang lengths of 4, 5, 6, and 7 bases are shown for samples 1) with and without antibody and 2) 1-hour and no incubation prior to the Cas12a cleavage reaction. Overhangs of 4 and 7 bases show similar fluorescence values for samples with and without antibody. Overhangs of 5 and 6 bases show a difference with antibody present, resulting in higher fluorescence levels generated at a quicker rate. B) All samples are compiled for both incubation parameters, 1 hour and no incubation. Graphs show that incubation duration prior to Cas12a cleavage reaction does not affect results.

Fluorescence Measurements: To acquire fluorescence measurements, the reporter strand is designed with a fluorophore (FAM) attached to the 3' end and a quencher (BHQ) attached to the 5' end of a poly-T DNA. As long as the ssDNA is intact, the quencher-fluorophore pair remain in close enough distance for Förster Resonance Energy Transfer to occur and fluorescence is quenched. Upon cleavage of the reporter, the quencher-fluorophore pair is separated, and fluorescence is induced. This signal is monitored using a plate reader over time (typically a period of 30 minutes). Using this process, we were able to observe the rate at which cleavage occurred depending on length of the sticky end overhang and presence/absence of antibody. As shown in FIG. 4A, the rate of cleavage (as evidenced by fluorescence) for overhang lengths of 4, 5, 6, and 7 bases varies depending on the presence or absence of antibody. Samples 5 and 6 show a difference in the rate of fluorescence increase with samples without the antibody being much slower compared to those with the antibody, indicating the necessity of antibody for Cas12a activation. These results show that samples can be tested using 5 and 6 base overhang lengths conjugated to a target antigen and results can be obtained within 15 minutes of cleavage reaction demonstrated by the drastic differences in fluorescence intensities at that time point between antibody-positive and antibody-negative samples.

Figure 4B:
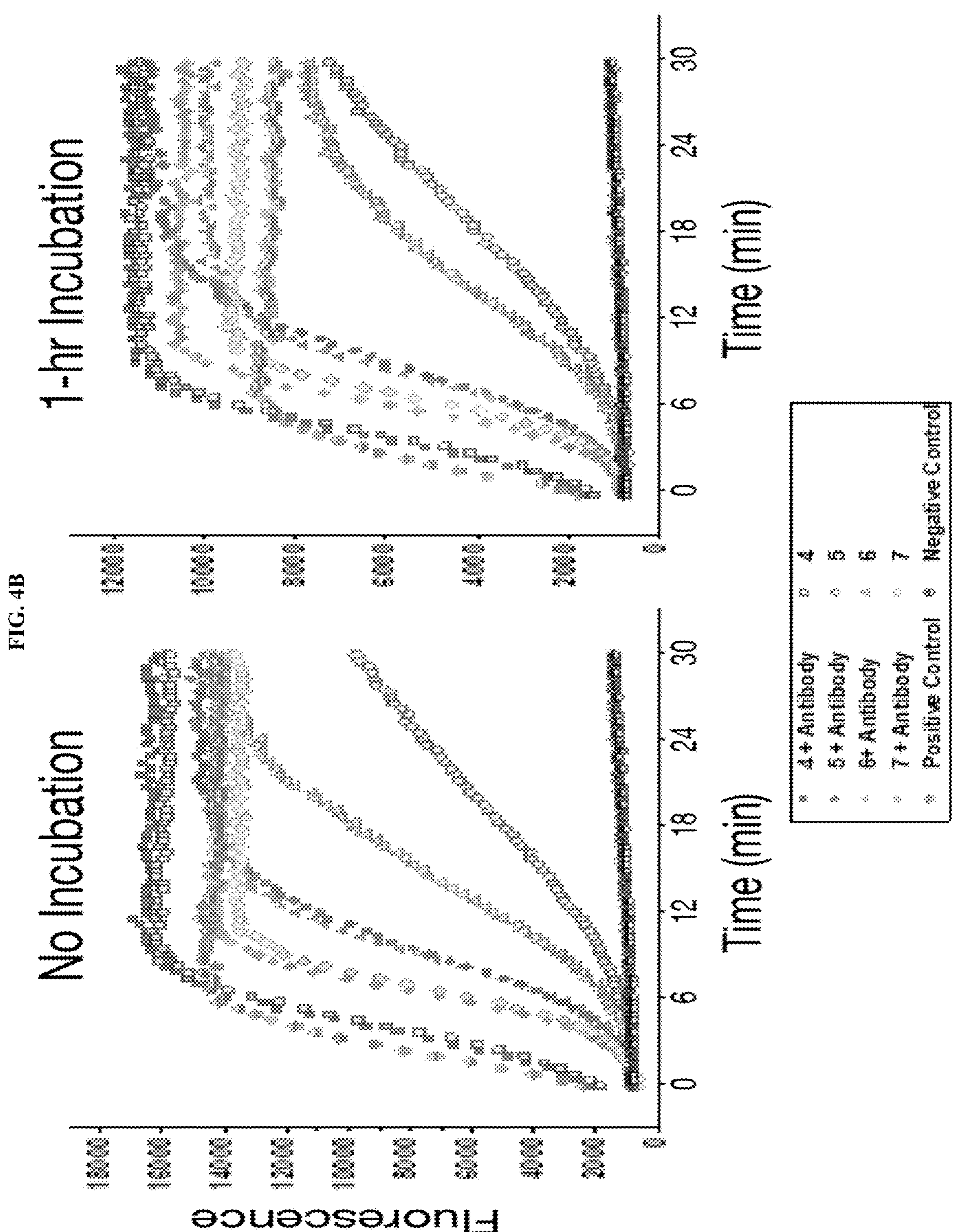

Two different incubation parameters for the antibody-target strand complex before cleavage, "no incubation" and "1-hour incubation," were also tested. FIG. 4B shows that for both incubation conditions, Cas12a was still activated and a difference in antibody/no antibody rates can be observed for overhang lengths 5 and 6 bases. Accordingly, sample incubation times will not be an issue.

Lateral Flow Assay: A lateral flow assay can be employed for readout of ssDNA state to implement tests amenable to point-of-care use. Lateral flow strips are cheap to manufacture, easily transported, easy/quick to test, and require no expensive or technical output equipment. The reporter ssDNA for readout was designed with two small molecules, biotin and FAM, on either end that interact with the lateral flow assay. The test uses commercial lateral flow strips (TwistDx, Ltd.) that contain a streptavidin line for binding to biotin along with gold nanoparticles decorated with anti-FAM antibodies. Without the antibody (no activation), intact reporter ssDNAs are captured by the biotin line and in turn capture the gold nanoparticles via the anti-FAM antibodies. Thus, inactivated Cas12a reactions will yield both a sample (streptavidin) line and a control line in the lateral flow strip. In the presence of the antibody, activation of Cas12a cleavage of the ssDNA reporters results in the formation of only a single band. FIG. 5 shows that for 6-base overhang, differences in band formation result from the antibody; with two bands for antibody-negative sample and one band for the antibody-positive sample as expected. This transition from fluorescence readout to a paper-based readout yields a convenient, easy-to-use design for diagnostics that remains flexible, requiring only the modification of reporter strands to fit the lateral flow assay.

In some cases, the lateral flow assay provided herein occurs on a lateral flow test device such as a lateral flow strip. Preferably, the lateral flow device comprises a sample contacting region that comprises (a) a plurality of single-stranded DNA (ssDNA) reporter constructs that comprise a first small molecule at the 5' end and a second small molecule at the 3' end of each ssDNA; (b) a Cas nuclease that exhibits collateral ssDNase or ssRNase activity; (c) a barcoded guide RNA comprising a spacer region, (d) a first synthetic nucleotide sequence comprising a first double-stranded DNA (dsDNA) target sequence and a first single-stranded DNA (ssDNA) protospacer adjacent motif (PAM) sequence, wherein the first synthetic nucleotide sequence is linked to a first antigen; and (e) a second synthetic nucleotide sequence comprising a dsDNA spacer sequence, a second dsDNA target sequence, and a second ssDNA PAM sequence, wherein the second synthetic nucleotide sequence is linked to a second antigen, wherein the first and second ssDNA PAM sequences comprise complementary sticky ends and form a double-stranded PAM (dsPAM) sequence when the first and second synthetic nucleotide sequences are brought into proximity by binding of the first and second antigens to an target molecule.

For Detection of Antibodies/Proteins: The methods described herein can be applied to the detection of a variety of different molecular analytes with the limiting factor being the identification of a small molecule, polypeptide, peptide, antibody, nanobody, etc., that binds specifically to the analyte and can be conjugated to a nucleic acid. It is worth mentioning that all binding immunoassays also require a molecule that binds specifically to the analyte.

The detection methods described in this disclosure can be used for identification of a broad range of infectious agents and diseases. Importantly, these methods can provide excellent sensitivity and multiplexing capability based on the amplification capabilities and the use of CRISPR nucleases. For instance, such assays can be used for the detection of human papillomavirus infection (HPV) related antibodies. HPV has been linked to multiple types of cancers including cervical and oropharyngeal cancer (OPC) and it has been demonstrated that circulating levels of an HPV-16 antibody correspond to pre-treatment and post-treatment OPC cases. It has also been shown that high levels of E6 antibody are associated with high reoccurrence risks for OPC. Such an antibody can be detected using our CRISPR-Cas method by conjugating target proteins or portions of proteins to target DNA. Other examples of potential antibody targets include HA-peptide antibody pairs from human influenza virus hemagglutinin protein and p17 binding peptide from HIV which have been successfully implemented in DNA-based circuits.

Proteins can also be detected using a similar setup. For instance, early stages of HIV-1 infection can be detected by targeting p24 proteins. P24 is found on the viral capsid of HIV particles and is one of the first detection markers for HIV in clinical use. This can be done by conjugating target strands to p24 nanobodies. These nanobodies are a tenth of the size of an antibody and recognize p24 with a 690 pM binding constant. Here the split strands can be conjugated to two different nanobodies. When multiple nanobodies bind p24 on the viral capsid, the strands will be brought into close proximity and hybridize activating CRISPR-Cas. There are about 2000 p24 copies per virus capsid accessible for binding and, when coupled with Cas multiple turnover ssDNase effect, can elicit a large response with detection of a single virus particle.

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a nucleic acid binding domain and a nucleic acid cleavage domain. In some embodiments, a protein comprises a proteinaceous part, e.g., an amino acid sequence constituting a nucleic acid binding domain, and an organic compound, e.g., a compound that can act as a nucleic acid cleavage agent.

Nucleic acids generally refer to polymers comprising nucleotides or nucleotide analogs joined together through backbone linkages such as but not limited to phosphodiester bonds. Nucleic acids include deoxyribonucleic acids (DNA) and ribonucleic acids (RNA) such as messenger RNA (mRNA), transfer RNA (tRNA), etc. Nucleic acids may be single-stranded, double-stranded, and also tripled-stranded.

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or include non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5 -methylcytidine, 2-aminoadeno sine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Figure 6:
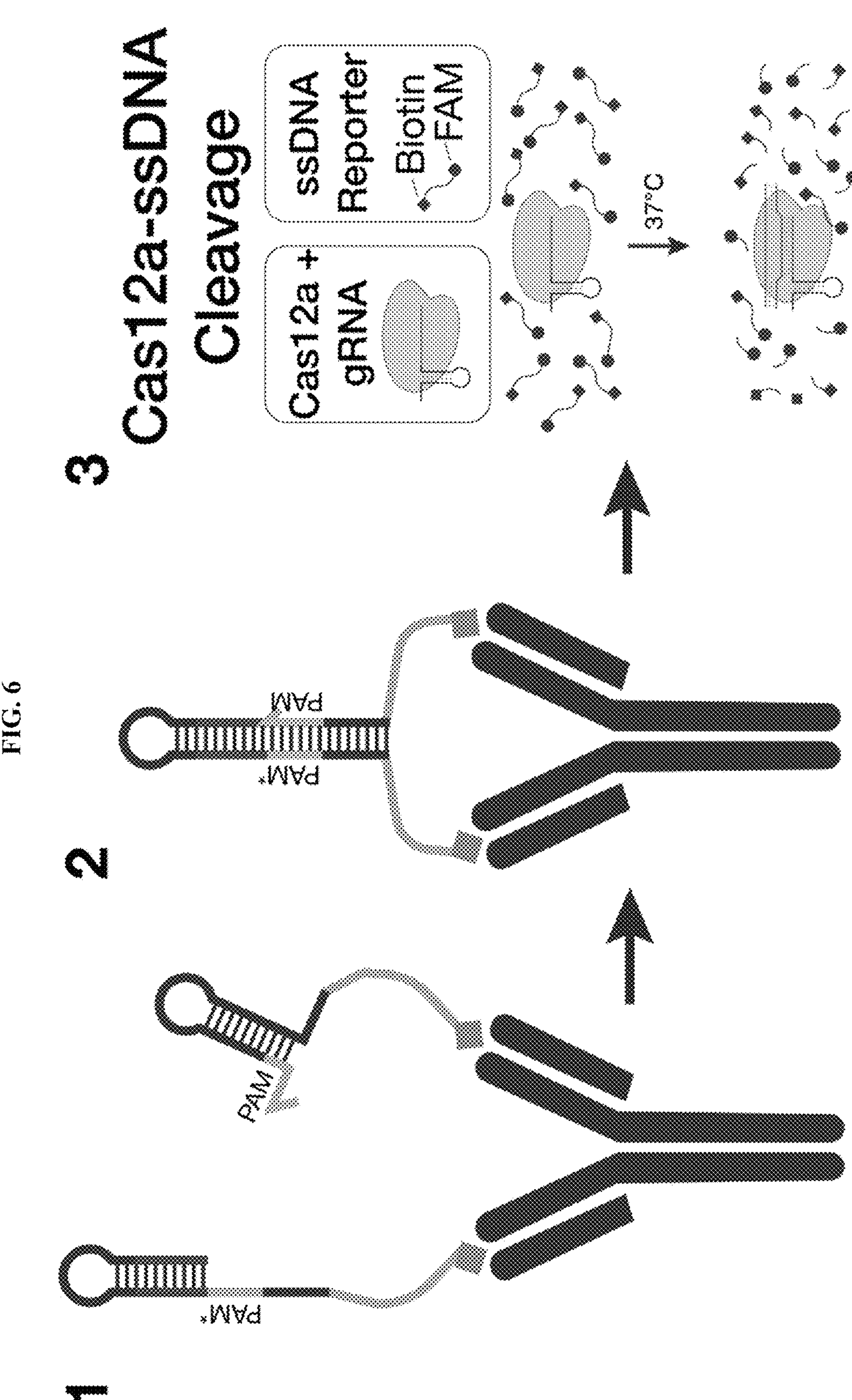
FIG. 6 is a schematic illustrating an alternative design for dsDNA target substrate formation. The PAM site on the strand not containing the spacer sequence is positioned within a toehold domain that is too short for spontaneous hybridization with the other strand. (Step 1) Binding to target antibody brings strands into close proximity. (Step 2) The co-localized PAM and PAM* sites hybridize and the ensuing branch migration process forms a stable target strand complex. (Step 3) The Cas12a/guide RNA complex is activated upon recognition of the target DNA and the ssDNA reporter strands are cleaved.

Alternative Designs: The conditional target dsDNA substrate design illustrated in FIG. 2 assembles the dsDNA target complex horizontally across the antibody arms. This configuration allows the split PAM sites to be in close proximity with a shorter ssDNA linker between the antigen and DNA. This design is optimal for antibody targets because of the 10-nm distance between binding sites. For other molecular targets such as proteins, viral capsids, or small molecules, the orientation of the double stranded complex can be altered to accommodate changes in geometry. FIG. 6 illustrates another embodiment in which the activated dsDNA complex is generated by forming a stem that lies in an orientation perpendicular to the one used previously. This design allows for more flexibility in terms of linker length and is compatible with target binding sites that may be further apart or separated by distances that are variable (e.g., viral capsid proteins). This design works by sequestering a portion of the PAM site in a hairpin on one strand, leaving a single-stranded toehold domain with a length of approximately 1 to 8 bases. This toehold is complementary to the PAM site and a single-stranded region on the other strand. When free in solution, the toehold domain is too short to base pair with the other strand, leaving CRISPR-Cas inactive. Upon binding to a target macromolecule, the two complementary strands are co-localized enabling toehold binding and branch migration through the complementary region. This interaction forms the complete dsDNA target sequence required to activate CRISPR-Cas enzyme. Alternative designs such as this afford another layer of control beyond the linker and overhang length to tune the system for different target macromolecules.

FIG. 7 illustrates general strand-displacement activation of CRISPR-Cas enzyme. In some cases, the method comprises (a) contacting to the sample a synthetic nucleotide sequence comprising a double-stranded DNA (dsDNA) spacer sequence lacking a PAM site and a first single-stranded DNA (ssDNA) toehold sequence, wherein the synthetic nucleotide sequence and target sequences are partially complementary, and wherein this interaction exposes a single-stranded DNA spacer sequence; (b) contacting the contacted sample of (a) to: (i) a Cas nuclease that exhibits collateral ssDNase or ssRNase activity, (ii) a guide RNA (gRNA), wherein the gRNA comprises the reverse complement of the ssDNA spacer sequence, and (iii) a single-stranded DNA or RNA reporter construct; whereby the gRNA forms a complex with the single-stranded DNA spacer sequence and the Cas nuclease cleaves the single-stranded DNA or RNA reporter construct; and (c) detecting cleavage of the single-stranded reporter construct, thereby detecting the presence of the target nucleic acid in the sample.

FIG. 9 illustrates another embodiment of methods for detecting a target molecule in a sample. As illustrated, the method can comprise (a) contacting to the sample (i) a first synthetic nucleotide sequence comprising a first double-stranded DNA (dsDNA) spacer sequence lacking a PAM site, a transcription-factor binding dsDNA sequence, and a first single-stranded DNA (ssDNA) toehold sequence, wherein the dsDNA is bound to a transcription factor that recognizes the target molecule; and a second synthetic nucleotide sequence comprising a single-stranded invading sequence, wherein the first and second synthetic sequences are partially complementary and interact when the transcription factor recognizes the small molecule and releases the first synthetic nucleotide sequence, and wherein this interaction exposes a single-stranded DNA spacer sequence; (b) contacting the contacted sample of (a) to: (i) a Cas nuclease that exhibits collateral ssDNase or ssRNase activity, (ii) a guide RNA (gRNA), wherein the gRNA comprises the reverse complement of the ssDNA spacer sequence, and (iii) a single-stranded DNA or RNA reporter construct; whereby the gRNA forms a complex with the single-stranded spacer sequence and the Cas nuclease cleaves the single-stranded reporter construct; and (c) detecting cleavage of the single-stranded reporter construct, thereby detecting the presence of the target molecule in the sample.

Figure 12:
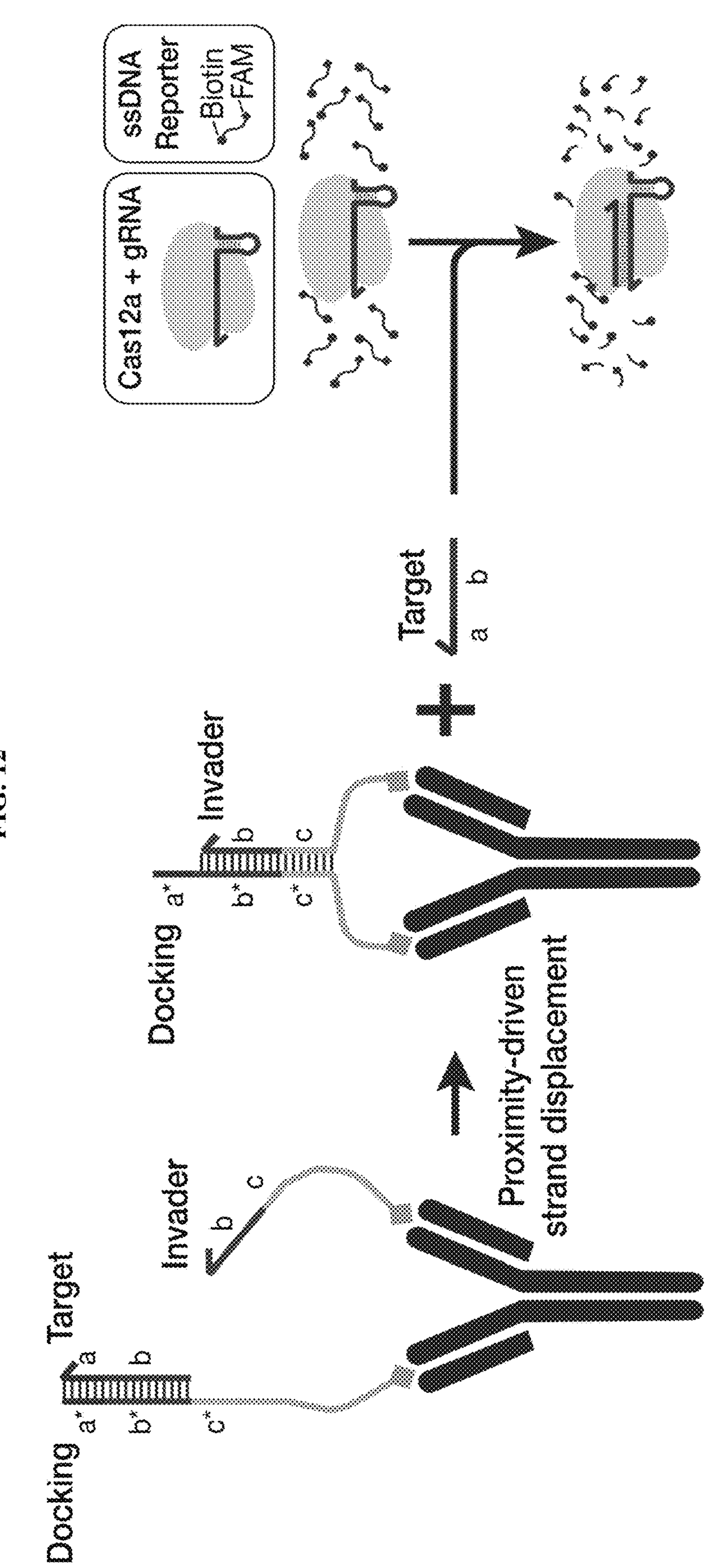
FIG. 12 illustrates proximity-driven strand-displacement for antibody detection with Cas12a. Peptide-conjugated DNAs containing epitopes for the target antibody are brought into close proximity upon antibody binding. Co-localization of the two DNAs promotes binding through a short toehold domain c* and enables release of the target DNA.

FIG. 12 illustrates another embodiment of methods for detecting a target molecule in a sample. As illustrated, the method comprises (a) contacting to the sample (i) a first synthetic nucleotide sequence comprising a first double-stranded DNA (dsDNA) target sequence lacking a PAM site and a first single-stranded DNA (ssDNA) toehold sequence, wherein the first synthetic nucleotide sequence is linked to a first antigen; and (ii) a second synthetic nucleotide sequence comprising a single-stranded invading sequence, wherein the second synthetic nucleotide sequence is linked to a second antigen, wherein the first and second sequences are partially complementary and interact when brought into proximity by binding of the first and second antigens to a target molecule, and wherein this interaction exposes a single-stranded DNA spacer sequence; (b) contacting the contacted sample of (a) to: (i) a Cas nuclease that exhibits collateral ssDNase or ssRNase activity, (ii) a guide RNA (gRNA), wherein the gRNA comprises the reverse complement of the ssDNA spacer sequence, and (iii) a single-stranded DNA or RNA reporter construct; whereby, in the presence of the target molecule that binds to the first and second antigens, the gRNA forms a complex with the ssDNA spacer sequence and the Cas nuclease cleaves the single-stranded reporter construct; and (c) detecting cleavage of the single-stranded reporter construct, thereby detecting the presence of the target molecule in the sample.

Applications: These tunable facets give not only an extensive choice of potential target molecules but also offer a wide range of applications. The same system can be used for multiple applications simply by modifying the report strand. Potential applications include but are not limited to clinical diagnostics, biomarker detectors, and cellular and tissue imaging tools. The ability to incorporate these systems into paper-based formats such as lateral flow assays also increases their applicability, making portable, easy-to-read diagnostic tools. This technology can also be combined with multiplexed reactions for detection of many different proteins/antibodies using barcoded target sequences. As used herein, "modifying" ("modify") one or more target nucleic acid sequences refers to changing all or a portion of a (one or more) target nucleic acid sequence and includes the cleavage, introduction (insertion), replacement, and/or deletion (removal) of all or a portion of a target nucleic acid sequence. All or a portion of a target nucleic acid sequence can be completely or partially modified using the methods provided herein. For example, modifying a target nucleic acid sequence includes replacing all or a portion of a target nucleic acid sequence with one or more nucleotides (e.g., an exogenous nucleic acid sequence) or removing or deleting all or a portion (e.g., one or more nucleotides) of a target nucleic acid sequence. Modifying the one or more target nucleic acid sequences also includes introducing or inserting one or more nucleotides (e.g., an exogenous sequence) into (within) one or more target nucleic acid sequences.

One advantage of the methods described herein is that they can be applied for the detection and identification of essentially any nucleic acid-containing organism. Accordingly, the pathogen can be virtually any pathogen or infectious agent (e.g., viruses, parasites, bacteria, fungi, prions) for which genetic information is available.

The term "detect" or "detection" as used herein indicates the determination of the existence, presence or fact of a target or signal in a limited portion of space, including but not limited to a sample, a reaction mixture, a molecular complex and a substrate including a platform and an array. Detection is "quantitative" when it refers, relates to, or involves the measurement of quantity or amount of the target or signal (also referred as quantitation), which includes but is not limited to any analysis designed to determine the amounts or proportions of the target or signal. Detection is "qualitative" when it refers, relates to, or involves identification of a quality or kind of the target or signal in terms of relative abundance to another target or signal, which is not quantified. An "optical detection" indicates detection performed through visually detectable signals: fluorescence, spectra, or images from a target of interest or a probe attached to the target.

Any isothermal amplification protocol can be used according to the methods provided herein. In some cases, isothermal amplification comprises NASBA (nucleic acid sequence-based amplification). Other isothermal amplification methods include: loop-mediated isothermal amplification (LAMP), strand displacement amplification (SDA), helicase-dependent amplification (HDA), nicking enzyme amplification reaction (NEAR), signal mediated amplification of RNA technology (SMART), rolling circle amplification (RCA), isothermal multiple displacement amplification (IMDA), single primer isothermal amplification (SPIA), recombinase polymerase amplification (RPA), and polymerase spiral reaction (PSR), which is described at nature.com/articles/srep12723 on the World Wide Web. In some cases, recombinase polymerase amplification (RPA) is used with the "one-pot" amplification and detection methods provided herein. In such cases, the methods comprise performing reverse transcription (RT), RPA, and transcription (TX) methods in a single test tube. In other cases, LAMP (loop-mediated isothermal amplification) is performed. As described in the Examples that follow, the unimolecular aptamer-based sensors described herein can bind directly to DNA LAMP amplification products. Alternatively, the amplification protocol is configured to add promoter sites to DNA LAMP amplification products such that each LAMP DNA can generate multiple RNA copies for improved assay effectiveness.

Nucleic acids and/or other moieties of the invention may be isolated. As used herein, "isolated" means to separate from at least some of the components with which it is usually associated whether it is derived from a naturally occurring source or made synthetically, in whole or in part.

Nucleic acids and/or other moieties of the invention may be purified. As used herein, purified means separate from the majority of other compounds or entities. A compound or moiety may be partially purified or substantially purified. Purity may be denoted by a weight by weight measure and may be determined using a variety of analytical techniques such as but not limited to mass spectrometry, HPLC, etc.

Any appropriate sample can be used according to the methods provided herein. In some cases, the sample is a biological sample obtained from an individual (e.g., a human subject, a non-human mammal). The sample is, in some cases, a diagnostic sample. The sample type will vary depending on the target pathogen. For example, diagnostic samples can be a serum sample, blood sample, sputum sample, urine sample, nasal sample, nasopharyngeal sample, throat swab sample, or other biological fluid. In some cases, serum samples have been frozen (e.g., at −80° C.) prior to testing. Samples appropriate for use according to the methods provided herein can also include, without limitation, food samples, drinking water, environmental samples, and agricultural products. In some cases, samples appropriate for use according to the methods provided herein are "non-biological" in whole or in part. Non-biological samples include, without limitation, plastic and packaging materials, paper, clothing fibers, and metal surfaces. In certain embodiments, the methods provided herein are used in food safety and food biosecurity applications, such as screening food products and materials used in food processing or packaging for the presence of pathogens in biological and/or non-biological samples.

Other applications for which the methods provided herein include, without limitation, profiling species in an environment (e.g., water); profiling species in an human or animal microbiome; food safety applications (e.g., detecting the presence of a pathogenic species, determining or confirming food source/origin such as type of animal or crop plant); obtaining patient expression profiles (e.g., detecting expression of a gene or panel of genes (e.g., biomarkers) to monitor the patient's response to a therapeutic regimen, to select a therapeutic regimen suitable for the patient, or to detect exposure of the patient to a toxin or environmental agent that affects expression of the gene or a panel of genes. As used herein, the terms "expressing," "expression," or "express" refer to the production of a gene product (e.g., an mRNA transcript from a nucleic acid sequence encoding thereof). As used herein, the terms "gene product" and "expression product" generally refer to an RNA transcribed from the gene or a polypeptide encoded by an RNA transcribed from the gene. Thus a regulatory element, environmental condition, stimulus, etc., that alters the level of transcription or the stability of an RNA transcribed from a gene or alters its ability to serve as a template for translation will be said to alter expression of the gene. Similarly, a regulatory element, environmental condition, stimulus, etc., that alters the level of translation or stability of a polypeptide translated from an RNA transcribed from the gene will be said to alter expression of the gene.

A "gene" is a sequence of nucleotides which code for a functional "gene product". Generally, a gene product is a functional protein. However, a gene product can also be another type of molecule in a cell, such as an RNA and more specifically either a tRNA or a rRNA. For the purposes of the present invention, a gene product also refers to an mRNA sequence which may be found in a cell. For example, measuring gene expression levels according to the invention may correspond to measuring mRNA levels. A gene may also comprise regulatory, non-coding, sequences as well as coding sequences. A variety of different gene expression protocols, including array-based protocols, are known to those of skill in the art.

In some cases, the device is used with a portable electronic reader. In this manner, the electronic reader serves as companion technology that provides robust and quantitative measurements of device outputs. In some embodiments, the electronic reader comprises readily available consumer components, open-source code, and laser-cut acrylic housing, and is powered by a rechargeable lithium ion battery. The electronic reader can further comprise an onboard data storage unit. In some cases, to achieve sensitive detection of toehold switch signal output, an acrylic chip that holds the freeze-dried, paper-based reactions is placed into the reader between a light source (e.g., to read optical density at excitation and emission wavelengths of light appropriate for and characteristic of a particular detectable reporter) and electronic sensors. In some cases, the light source is a light emitting diode (LED) or organic light emitting diode (OLED) light source. Samples can be read using onboard electronics. In this manner, a portable electronic reader can provide low-noise measurements of changes associated with the reporter element including changes in light transmission due to LacZ-mediated color change.

In certain embodiments, provided herein is a device for identifying a pathogen-associated nucleic acid, comprising a preserved paper test article, wherein the methods described herein are performed using the preserved paper test article. In some cases, the paper test article is preserved by freeze-drying.

Articles of Manufacture

In another aspect, the present invention provides articles of manufacture useful for performing a lateral flow assay according to the methods provided herein. In certain embodiments, the article of manufacture is a kit comprising a lateral test flow device provided herein. In some cases, the kit also comprises instructions for performing the detection methods provided herein. In some cases, the kit further comprises a means for detecting cleavage of a single-stranded DNA reporter construct.

In certain embodiments, the article of manufacture is a kit comprising reagents (i.e., ingredients) to carry out the methods of this disclosure, with or without a lateral flow device of this disclosure. In some cases, the kit also comprises instructions for performing the detection methods provided herein. In some cases, the kit further comprises a means for detecting cleavage of a single-stranded DNA reporter construct.

Unless defined otherwise, all technical and scientific terms used herein have the same meaning as commonly understood by one of ordinary skill in the art to which the embodiments pertains. So that the compositions, methods, and systems provided herein may more readily be understood, certain terms are defined:

As used in this specification and the appended claims, the singular forms "a," "an," and "the" include plural references unless the context clearly dictates otherwise. Any reference to "or" herein is intended to encompass "and/or" unless otherwise stated.

The terms "comprising", "comprises" and "comprised of as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

All references, patents and patent applications disclosed herein are incorporated by reference with respect to the subject matter for which each is cited, which in some cases may encompass the entirety of the document.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

In preferred embodiments, the terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold, and more preferably within 2-fold of a given value. Numerical quantities given herein are approximate unless stated otherwise, meaning that the term "about" or "approximately" can be inferred when not expressly stated.

The invention will be more fully understood upon consideration of the following non-limiting Examples.

EXAMPLES

Multiplexable, Multianalyte Detection via Coupled Nucleic Acid Strand Displacement and CRISPR/Cas Recognition Described in this example is a new sensing platform that makes use of CRISPR-Cas12a single-stranded DNA (ssDNA) recognition and DNA strand displacement to provide better performance and improved programmability without limiting the breadth of potential target analytes.

The Cas12a enzyme has the capacity to bind to ssDNA targets that are complementary to its guide RNA (gRNA) spacer sequence. Upon ssDNA binding, Cas12a cuts its bound ssDNA target and the collateral cleavage activity of the enzyme is activated, initiating indiscriminate degradation of other ssDNAs that come into contact with the enzyme and making it compatible with the same readouts as the dsDNA-based systems described above. Unlike dsDNA substrates, however, ssDNAs that activate Cas12a do not require a protospacer adjacent (PAM).

Figures 7A, 7B:
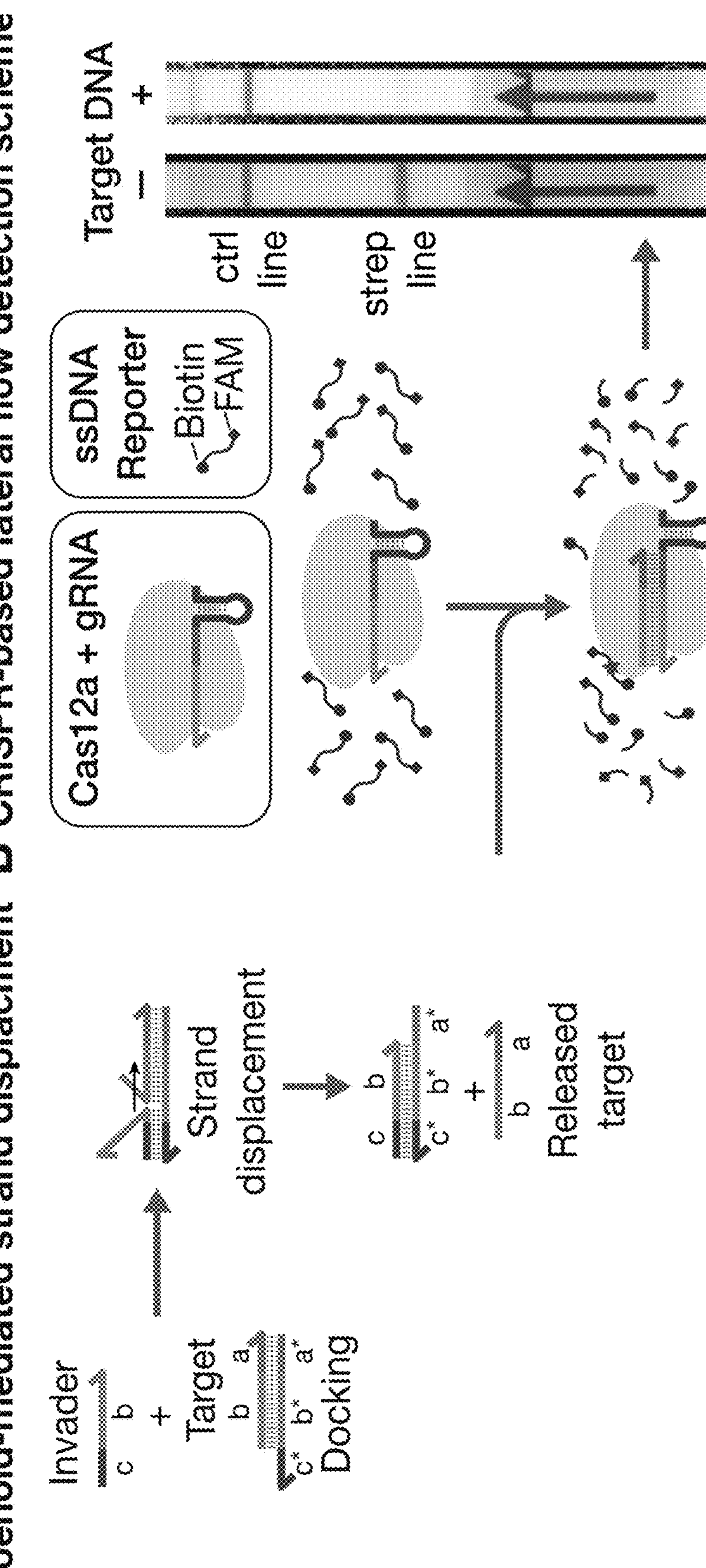
FIGS. 7A-7B illustrate strand-displacement driven activation of CRISPR-Cas12a. A, The target ssDNA (comprising domains b and a), which is recognized by the Cas12/gRNA complex, is initially sequestered from the enzyme within a DNA duplex with the docking strand. The DNA duplex lacks a PAM site adjacent to the target site to prevent initial Cas12a/gRNA recognition. The invader strand (comprising domains c and b) initiates binding with the dock through toehold-domain c*, and the ensuing strand-displacement reaction leads to the release of the target ssDNA. B, The released target is able to activate the Cas12a/gRNA and its collateral ssDNase activity. ssDNA reporter strands containing biotin and FAM at the ends are cleaved by the enzyme. Cleaved products are unable to form a purple band at the streptavidin (strep) band, indicating a positive assay result.

To take advantage of the ssDNA detection capabilities of Cas12a for molecular recognition, a first system that employs toehold-mediated strand displacement to control Cas12a activation was engineered as shown in FIG. 7A. The target ssDNA in the system contains a sequence with the domains b-a. This target ssDNA is the substrate for the Cas12a/gRNA complex when the gRNA contains the spacer sequence a*-b*, where "*" is used to designate the reverse complement sequence. Initially, the target ssDNA is not free in solution and is hybridized to a docking strand. Importantly, the resulting dsDNA complex between target and docking strand is unable to activate Cas12a because it lacks the PAM site required for CRISPR dsDNA recognition. The docking strand also contains an overhanging single-stranded region (domain c*) called a toehold. To activate the system, a third DNA strand referred to as the invader sequence with the sequence c-b initiates binding through the toehold domain. As used herein, the term "invader sequence" refers to a single-stranded DNA sequence that comprises domains c and b as described herein, where domain b of the invader sequence is the same as domain b of the target strand. In some embodiments, the invader sequence comprises sequence (e.g., domain b) derived from the target molecule to be detected. In some cases, the invader sequence is derived from sequence of a virus or other pathogen or from a patient genome. A subsequent branch migration reaction displaces the b domain of the target strand from the docking strand. This step means that the target strand is only tethered to the docking strand by the a domain. This a domain is designed to be sufficiently short (i.e., with a low enough melting temperature) to spontaneously separate from the docking strand. Alternatively, it has the potential to be removed by the complementary gRNA spacer sequence. In either case, the target strand is ultimately released from the docking strand and free to be recognized by the Cas12a/gRNA complex. Following recognition, the activated collateral cleavage of Cas12a can be monitored in the same way as previously proposed designs using an ssDNA probe specific for fluorescence or lateral flow readout (FIG. 7B). It is also important to note that the ssDNA invader strand is designed to not directly activate the Cas12a/gRNA complex. Although the invader shares the common domain b with the target strand, domain a in the system is designed to be sufficiently long and located in the seed region for Cas12a sequence recognition so that hybridization with domain b alone cannot activate the enzyme.

Strand Displacement Design Considerations: Studies were conducted to determine the optimal domain lengths required to implement the strand-displacement Cas12a activation systems described above. The three domains a, b, and c must adopt dimensions that promote efficient strand-displacement reactions while still ensuring Cas12a is not activated by the invader DNA strand. Furthermore, the forward toehold c and reverse toehold a lengths must be tuned to promote invader binding via domain c and release of the displaced target DNA via domain a. We summarize below the main design considerations and findings.

In general, the toeholds can vary in length from 1-15 bases and it is also worth noting that the lengths of both toeholds can differ from each other. The length of b, which is the common domain of the target and invader, is limited to the longest sequence that overlaps with the spacer but is unable to activate Cas12a. To determine optimal domain b lengths, shortened target ssDNA sequences designed to mimic the b domain of the invader were exposed to a Cas12a complexed with a gRNA having a 24-nt spacer sequence. From these experiments, we determined that b needed to be 15, 14, or fewer nucleotides to prevent activation when it contained the target sequence truncated from the 3' end. When the target sequence was truncated from the 5' end, we found that the b domain required shorter lengths of 12, 11, or fewer nucleotides to prevent Cas12a activation. These findings led us to choose the strand displacement polarity shown in FIG. 1 where displacement occurs in the 5' to 3' direction, since this enabled the b domain to be longer (up to 15 nts) and accommodated shorter reverse toehold lengths in domain a to encourage spontaneous release of the target DNA following invader binding.

The initial strand displacement was found to be optimal using b domains with a length of 15 nts and a and c domains having lengths of 9 nts. Other toehold lengths were tested, and activation still occurred so the toehold length can vary. We also tested 24 different sequences of a, b, and c domains in strand-displacement systems to ensure no sequence restraints existed. Of these, all displacement reactions worked but some showed detectable levels of nonspecific activation, indicating that the target was getting displaced in low concentrations without the invader.

Figure 8:
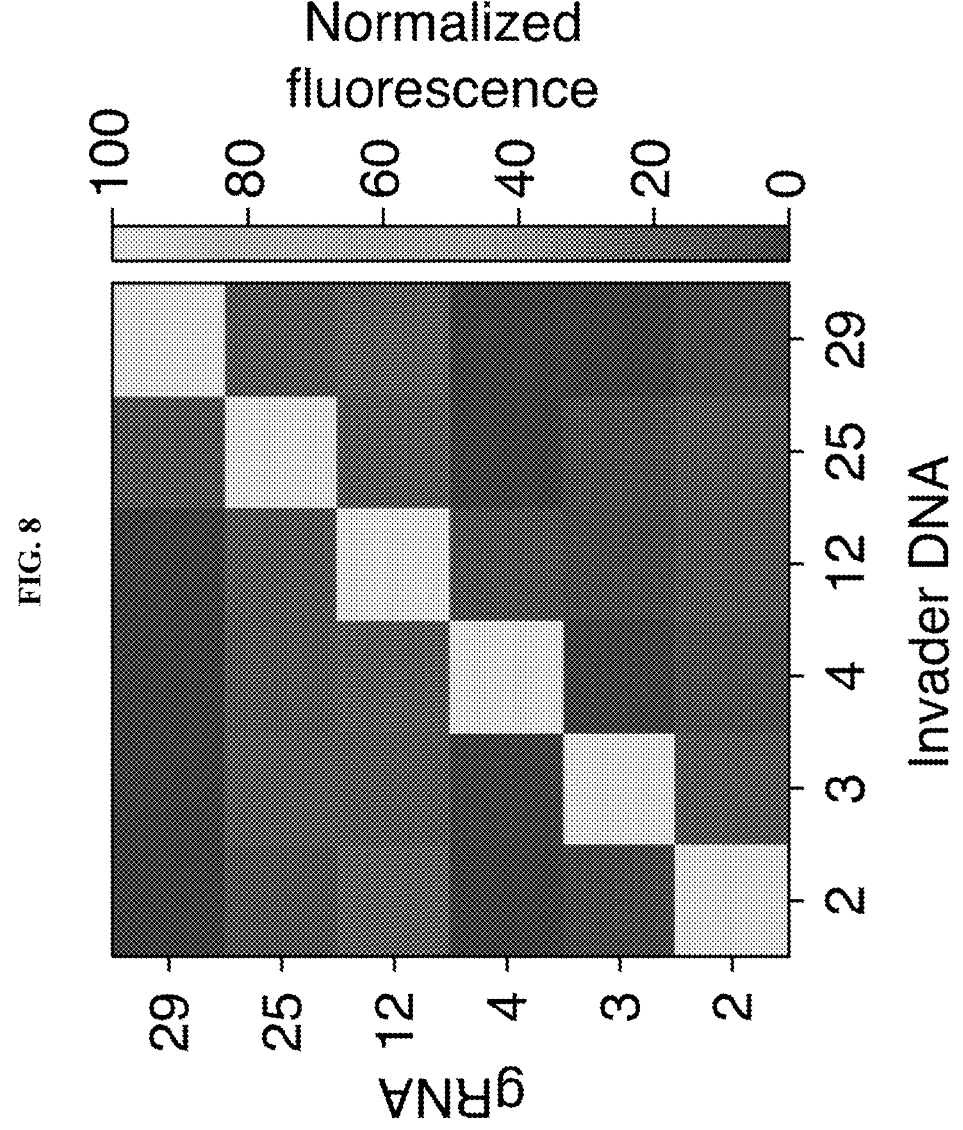
FIG. 8 demonstrates validation of orthogonal strand-displacement-based CRISPR-Cas12a activators. A library of six orthogonal strand-displacement systems were tested using different combinations of invader DNA and gRNA. Only when cognate invader and gRNA sequences are used is a strong fluorescent reporter signal produced through CRISPR-Cas12a cleavage.

Validating Orthogonal Libraries of Cas12a Strand-Displacement Activators: For the systems that showed negligible nonspecific activation, we tested them in combined reactions to assess their orthogonality. In principle, orthogonal strand-displacement systems should only activate when the invader DNA is paired with a Cas12 complexed with its cognate gRNA. FIG. 8 shows experimental data from testing a set of six putatively orthogonal systems based on analysis of their sequences. In these experiments, an invader DNA is added to the reaction and used to release its cognate target DNA from the docking strand. The reaction products are then supplied to different CRISPR-Cas12a reactions containing gRNAs with different spacer sequences. In the reactions where cognate invader DNA and gRNA are used, collateral cleavage is activated, producing a strong fluorescence from the cleavage of short reporter ssDNAs with fluorophore-quencher end modifications. However, when the invader DNA and gRNA do not match, low fluorescence is observed in the reactions. As shown in FIG. 8, we find the strongest fluorescence in reactions where cognate invader DNA and gRNA are used and we observe low fluorescence elsewhere, demonstrating the orthogonality of the set. Although these experiments only demonstrate that independent DNAs can be detected using the strand-displacement systems, such orthogonal sets can be used to detect combinations of different target analytes using the small molecule and protein detection approaches described below. Based on specificity of both strand-displacement reactions and Cas12/gRNA sequence recognition, it should be possible to multiplex dozens or perhaps even hundreds of detection reactions simultaneously using our approach.

Figures 9A, 9B:
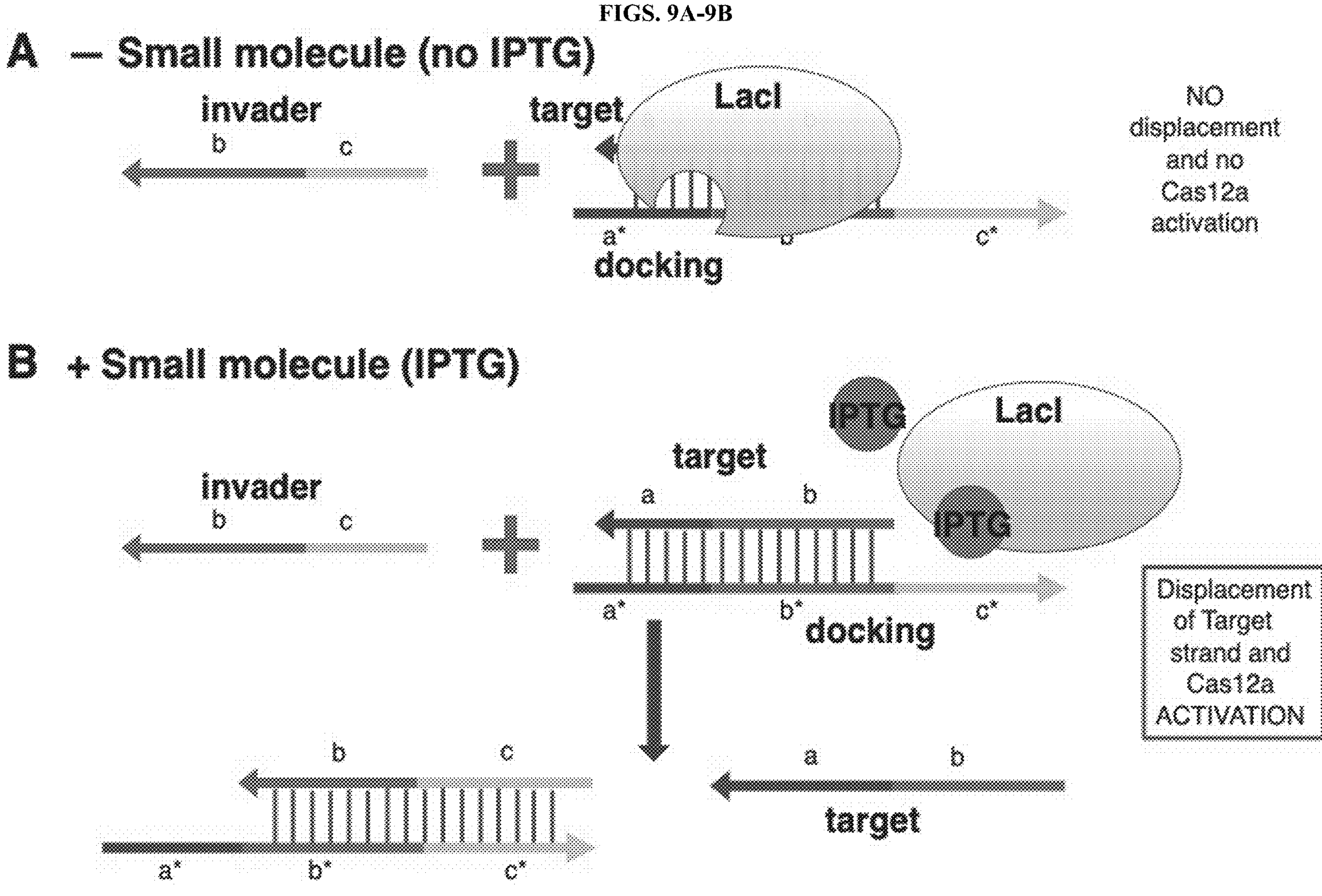
FIGS. 9A-9B illustrate small-molecule detection mechanism using the lac repressor (Lad) transcription factor. A, In the absence of the small molecule ligand IPTG, Lad binds to its cognate DNA binding sequence, which is contained in domain b, in the target-docking strand complex. The bound Lad prevents strand invasion by the invader so that the target DNA is not released and Cas12a is not activated. B, Upon addition of the small molecule ligand, IPTG binds to Lad and the transcription factor releases the target-docking strand complex. The invader can then complete the strand-displacement process to release the target DNA. The target DNA then activates the Cas12a/gRNA complex and in turns cleaves the ssDNA reporters.

Scheme for Small Molecule Detection Using Transcription Factors: The strand-displacement systems can be applied to the detection of small molecule analytes using transcription factors that bind to and block displacement of the target strand. Transcription factors are proteins used to control transcription of genes depending on environmental conditions. They do this by directly binding to DNA sequences to turn on/off gene expression at the appropriate time. This is often done in response to a small molecule analyte that binds to the transcription factor, either promoting or inhibiting protein binding to the DNA binding domain. By incorporating transcription-factor-specific DNA binding domains into our target sequence strands, transcription factors can be used to bind to the target-docking complex, blocking interactions with the invading strand (FIG. 9A). The small molecule analyte is then introduced, causing the transcription factor to unbind the DNA complex (FIG. 9B). Once this occurs, the invading strand is free to displace the target strand, and this can be monitored using lateral flow or fluorescence readout.

An advantage to this approach is that we are able to sidestep conjugating protein/small molecules to DNA by taking advantage of proteins that readily interact with specific DNA binding domains. These protein/DNA complexes form spontaneously and can be manipulated with the introduction of a small molecule analyte. The small molecule analyte can either promote binding or inhibit it. Another benefit to this approach is that transcription factors are found throughout nature and can act as repressors or activators for a diverse range of molecules. This means that this design can be applied to detection of different molecules spanning metals to hormones.

Figures 10A, 10B:
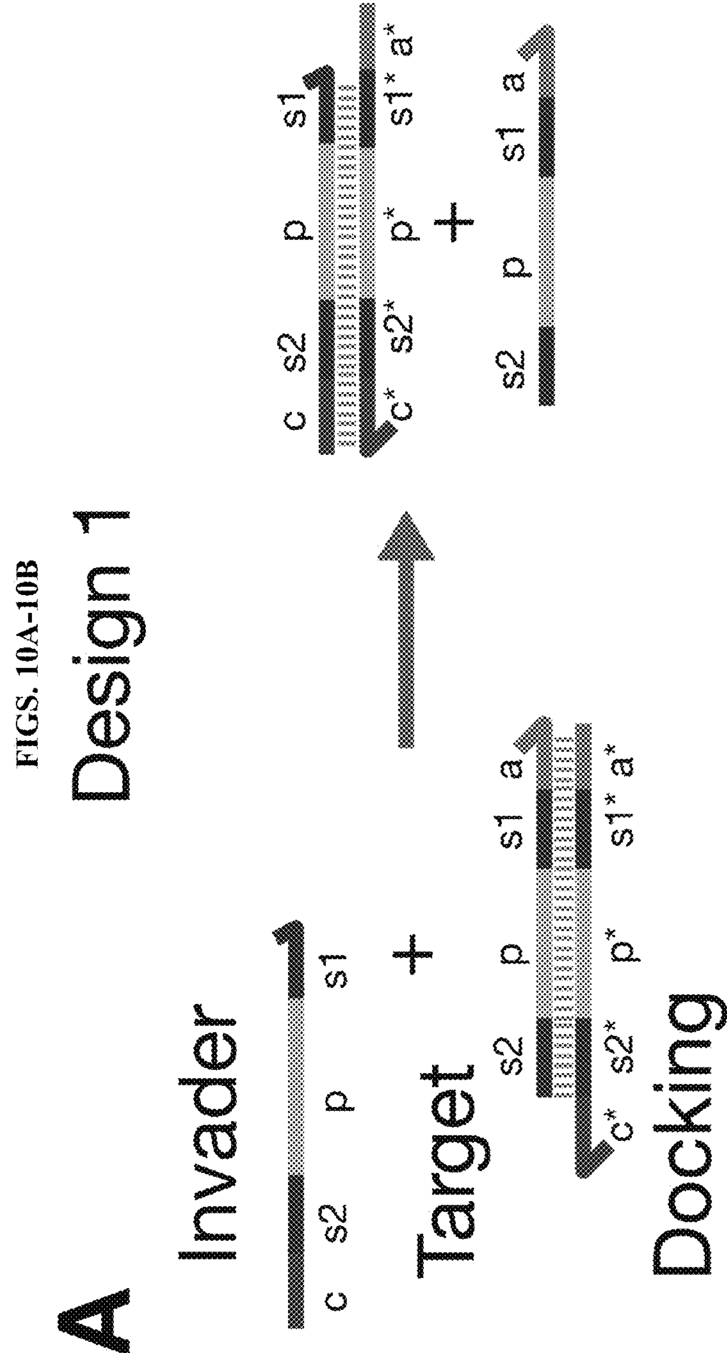
FIGS. 10A-10B illustrate DNA strand-displacement designs used for transcription-factor-based sensors. A, Domain-level diagram of the invader, target, and docking strands used for Design 1. B, Domain-level diagram of the invader, target, and docking strands used for Design 2. For both designs, the gRNA spacer sequence is complementary to a 24-nt region starting from the 3' end of the target DNA. For Designs 1 and 2, the center of the strand contains the promoter region p to which the target transcription factor binds.

Transcription Factor Strand Displacement Design: Two designs were built off of the initial strand displacement design for transcription-factor-based small molecule detection. Design 1 contains a and c reverse and forward toehold domains, respectively, each with a length of 9 nucleotides (FIG. 10A). The b domain now contains multiple elements. The center of the strand contains the promoter region p to which the target transcription factor binds. The promoter length varies from 11-46 nucleotides in our current systems but can be adjusted as needed. On either side of the p domain, we added 6-nucleotide spacer domains denoted as s1 and s2 to ensure the promoter sequence remain double-stranded upon hybridization of the target and docking strands. From this target strand sequence, the spacer region for Cas12a activation consists of the last 24 nts on the 3' end of the target DNA. This spacer region generally comprises the domains a, s1, and a portion of p.

Design 2 makes use of previously validated orthogonal strand-displacement systems (e.g., FIG. 8) to enable reuse of existing gRNAs, facilitate future multiplexed small molecule detection, and increase the yield of functional sensors. Validated orthogonal domains b and a are incorporated in the target DNA at the 3' end of the promoter sequence p (FIG. 10B). As a result of this change, release of the target DNA by the invader produces a Cas12a target sequence b-a that is already known to specifically activate the CRISPR enzyme complexed with the cognate gRNA, which simplifies screening. Further, it is expected to provide low crosstalk with other target sequences taken from the orthogonal library. For Design 1, in contrast, use of the promoter sequence in the released target DNA could lead to unwanted crosstalk depending on the sequences of the other promoters used in a multiplexed reaction. On the 5' end of the promoter p, a spacer region s2 of 6 nts is used to ensure the full promoter sequence is in double-stranded form when the target and docking strand are hybridized. In experiments, we found that both Design 1 and Design 2 provided multiple functional sensors.

Figures 11A, 11B:
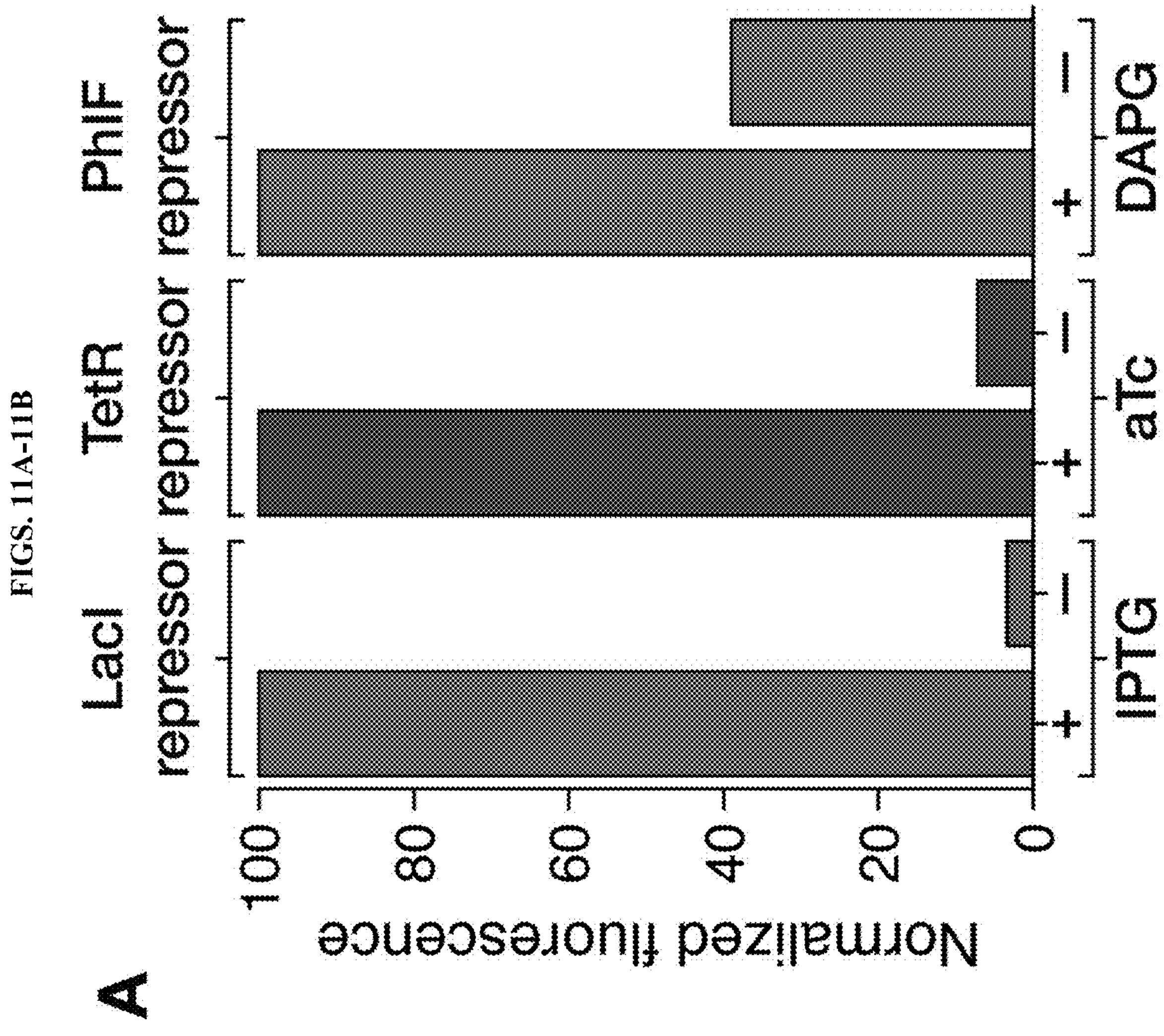
FIGS. 11A-11B present small molecule detection using transcription factors. A, Strand-displacement systems containing DNA binding domains for the lac repressor (LacI), tet repressor (TetR), and PhIF enable detection of IPTG, aTc, and DAPG, respectively. Upon introduction of the small molecule analyte, the repressor releases the bound DNA to allow strand displacement by the invader strand. The displaced target strand activates Cas12a, enabling detection through cleavage of fluorescent ssDNA reporters. B, The detection limit was tested for the TetR-aTc system. The highest fluorescence is observed in the positive control (PC) containing no transcription factor or small molecule. A significantly higher fluorescence level is observed for aTc concentrations ranging from 200 nM down to 200 fM compared to the reaction lacking aTc.

Validation of Transcription-Factor-Based Small Molecule Detection: We have demonstrated the ability to use this method to detect three different small molecules using three different transcription factors. The first example used the lac repressor (Lad) transcription factor found in *E. coli*. This protein represses transcription of genes necessary to break down the sugar lactose. In the presence of high lactose, the repressor is released from the DNA binding domain, and transcription occurs. The small molecule isopropyl β-D-1-thiogalactopyranoside (IPTG), a lactose analog, can also be used to displace the lac repressor. Here, we have demonstrated that in the presence of IPTG, the transcription factor is removed from the target-docking complex, and displacement of the target strand occurs. From here, the target activates the Cas12a enzyme and the readout is measured using a fluorescence plate reader. In FIG. 11A, there is a 30-fold increase in fluorescence output when the small molecule analyte IPTG is introduced compared to without. The second example uses a tet repressor (TetR) and is displaced with anhydrotetracycline (aTc) showing that the design is applicable to multiple small molecule analytes. The tet repressor responds to a family of tetracyline antibiotics and thus makes a range of important antibiotic analytes compatible with the detection platform. The third example uses a PhIF repressor found in *Pseudomonas fluorescens* to regulate an antifungal compound, 2,4-diacetylphoroglucinol (DAPG). FIG. 11A shows a 2.6-fold increase in fluorescence signal with the DAPG positive sample compared to the sample without DAPG.

The tet repressor system was then used to explore the detection limits for transcription-factor mediated small molecule detection strategy. Using a titration of aTc starting from 200 nanomolar to 200 femtomolar, we characterized the fluorescence as a function of the concentration of the small molecule. FIG. 11B shows the fluorescence values for seven different concentrations of aTc, including no aTc. Results show a 2.6-fold increase in signal from no aTc to 200 femtomolar aTc and a 4.5-fold with 200 nanomolar aTc. This indicates we can use this platform for femtomolar detection of various small molecules. In comparison, the tet repressor provides a detection limit of ~1 nM in gene expression assays in *Escherichia coli* [A. J. Meyer et al., *Nature Chem. Biol.* 15, 196-204 (2019)]. Thus, the CRISPR-Cas strategy for small molecule detection provides a greater than 1000-fold improvement in assay sensitivity.

Proximity-driven strand-displacement detection: The system described herein can also be employed to detect a broad range of analytes using proximity-driven strand-displacement reactions. In this mode of detection, recognition of the target analyte by two DNA systems modified with molecular recognition elements (e.g., peptides, antibodies, aptamers, small molecule ligands) brings the two DNA systems into close proximity to promote a strand displacement reaction. An implementation of such a system using peptides as molecular recognition elements for antibody detection is shown in FIG. 6. The two DNA systems are both conjugated to peptides that contain the epitopes for the antibody of interest. One of the DNAs consists of the docking strand and the bound target. The other comprises the invader DNA. The two DNA systems can interact via the toehold domain c*; however, the toehold is designed to be sufficient short, typically 1 to 5 nts, to prevent spontaneous hybridization in the absence of the antibody analyte. When the antibody is added to the system, both DNA systems can bind to the antibody arms. This co-localization facilitates interaction through the c-c* domains and enables the invader to displace the target strand. The released target strand can then be detected using Cas12a complexed with cognate gRNA, enabling detection through colorimetric or fluorimetric measurement. This proximity-driven approach can be used to detect a variety of small molecule, protein, and antibody analytes and is highly multiplexable based on the specificity of strand displacement and CRISPR nucleic acid recognition.

Potential Application: Utilizing this CRISPR/Cas system coupled with strand exchange to detect small molecules provides a very dynamic, versatile, and easy-to-use detection method. This is largely due to the vast numbers and types of transcription factors available, spanning metal detection to antibiotic and drug detection. Considering this, and with the ability to couple readout to a paper based lateral flow assay, potential applications include testing for water purity with the ability to detect arsenic, lead, copper, and other dangerous/unwanted metals. With the built-in amplification of CRISPR/Cas collateral cleavage, we can expect to have low, relevant detection limits on paper-based devices that are cheap to make and easy to use. This method also has the potential to be used for clinical applications with the ability to detect various types of drugs such as antibiotics and the date-rape drug gamma-Hydroxybutyric acid (GHB), and hormones such as estrogen; being limited only to finding small molecules with corresponding transcription factors. A similarly diverse set of analytes, including antibodies and other protein biomarkers, can be detected using the proximity-driven detection scheme described in FIG. 12.

The present invention has been described in terms of one or more preferred embodiments, and it should be appreciated that many equivalents, alternatives, variations, and modifications, aside from those expressly stated, are possible and within the scope of the invention.

We claim:

1. A method of detecting a target molecule in a sample, the method comprising the steps of:

(a) contacting to the sample a first synthetic nucleotide sequence comprising a first double-stranded DNA (dsDNA) spacer sequence and a first single-stranded DNA (ssDNA) sequence that is reverse complementary to a protospacer adjacent motif (PAM) sequence, wherein the first synthetic nucleotide sequence is linked to a first antigen; and a second synthetic nucleotide sequence comprising a single-stranded sequence or a dsDNA sequence and a ssDNA PAM sequence, wherein the second synthetic nucleotide sequence is linked to a second antigen, wherein the first ssDNA and the second ssDNA PAM sequences comprise complementary sticky ends and form a double-stranded PAM (dsPAM) sequence when the first and second synthetic nucleotide sequences are brought into proximity by binding of the first and second antigens to the target molecule, and wherein the reverse complementary ssDNA PAM sequence is adjacent to the reverse complement of the spacer sequence in the first synthetic nucleotide;

(b) contacting the contacted sample of (a) to:

(i) a Cas nuclease that exhibits collateral ssDNase or ssRNase activity, (ii) a guide RNA (gRNA), wherein the gRNA comprises the spacer sequence, and (iii) a single-stranded DNA or RNA reporter construct;

whereby, in the presence of the target molecule that binds to the first and second antigens, the gRNA forms a complex with the dsPAM sequence and the dsDNA spacer sequence and the Cas nuclease cleaves the single-stranded reporter construct; and (c) detecting cleavage of the single-stranded reporter construct, thereby detecting the presence of the target molecule in the sample.

2. A method for producing a barcoded gRNA by:

(a) contacting to a sample a first single-stranded DNA (ssDNA) sequence comprising a first gRNA barcode region and a first stem-forming region, wherein the first stem-forming region is linked to a first antigen, and a second ssDNA sequence comprising a second gRNA barcode region, a third gRNA barcode region, and a second stem-forming region having a sequence complementary to that of the first stem-forming region, wherein the second stem-forming region is linked to a second antigen, whereby, in the presence in the sample of an antibody that binds specifically to antigens of the first and second ssDNA sequences, the first and second stem-forming regions form a double-stranded DNA region;

(b) contacting to the contacted sample of (a) a split DNA template that comprises (i)) a 5' phosphorylated strand having a hairpin structure that comprises a single-stranded hairpin domain sequence, a double-stranded T7 promoter sequence, and ssDNA sequences complementary to the first and second gRNA barcode regions, and (ii) a single DNA strand comprising a sequence complementary to the third gRNA barcode region, whereby, in the presence of DNA ligase and DNA polymerase, an extended double-stranded DNA sequence is obtained that comprises a double-stranded T7 promoter sequence, a double-stranded gRNA barcode region, and a double-stranded hairpin domain that encodes a conserved gRNA hairpin; and (c) contacting the extended double-stranded DNA sequence of (b) to T7 RNA polymerase, whereby a gRNA comprising first, second, and third barcodes is produced.

3. A method for producing a barcoded gRNA by:

(a) contacting to a sample a first single-stranded DNA (ssDNA) sequence comprising a first gRNA barcode region and a first stem-forming region, wherein the first stem-forming region is linked to a first protein-binding probe, and a second ssDNA sequence comprising a second gRNA barcode region, a third gRNA barcode region, and a second stem-forming region having a sequence complementary to that of the first stem-forming region, wherein the second stem-forming region is linked to a second protein-binding probe, whereby, in the presence in the sample of one or more proteins that bind specifically to protein-binding probes of the first and second ssDNA sequences, the first and second stem-forming regions form a double-stranded DNA region;

(b) contacting to the contacted sample of (a) a split DNA template that comprises (i) a 5' phosphorylated strand having a hairpin structure that comprises a single-stranded hairpin domain sequence, a double-stranded T7 promoter sequence, and ssDNA sequences complementary to the first and second gRNA barcode regions, and (ii) a single DNA strand comprising a sequence complementary to the third barcode region, whereby, in the presence of DNA ligase and DNA polymerase, an extended double-stranded DNA sequence is obtained that comprises a double-stranded T7 promoter sequence, a double-stranded gRNA barcode region, and a double-stranded hairpin domain that encodes a conserved gRNA hairpin; and (c) contacting the extended double-stranded DNA sequence of (b) to T7 RNA polymerase, whereby a gRNA comprising the first, second, and third barcodes is produced.

4. The method of claim 1, wherein the target molecule is an antibody.

5. The method of claim 1, wherein the Cas nuclease is Cas12a, Cas13a, Cas13b, Cas13d, Cas12g1, or Cas12i1.

6. The method of claim 1, wherein the single-stranded reporter construct comprises a first small molecule at the 5' end and a second small molecule at the 3' end.

7. The method of claim 6, wherein the first and second small molecules are selected from biotin and FAM (fluorescein).

8. The method of claim 1, wherein the first ssDNA and the second ssDNA PAM sequences comprise complementary sticky ends having a length of 5 or 6 base pairs.

9. The method of claim 1, wherein the first ssDNA and the second ssDNA PAM sequences comprise complementary sticky ends having a length of 3 to 6 base pairs.

* * * * *